(12) United States Patent
Benary

(10) Patent No.: US 9,101,457 B2
(45) Date of Patent: Aug. 11, 2015

(54) ENDOVASCULAR STENT-GRAFT SYSTEM WITH FENESTRATED AND CROSSING STENT-GRAFTS

(75) Inventor: Raphael Benary, Tel Aviv (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 659 days.

(21) Appl. No.: 13/514,240

(22) PCT Filed: Dec. 8, 2010

(86) PCT No.: PCT/IL2010/001037
§ 371 (c)(1),
(2), (4) Date: Sep. 21, 2012

(87) PCT Pub. No.: WO2011/070576
PCT Pub. Date: Jun. 16, 2011

(65) Prior Publication Data
US 2013/0013051 A1    Jan. 10, 2013

Related U.S. Application Data

(60) Provisional application No. 61/267,453, filed on Dec. 8, 2009.

(51) Int. Cl.
*A61F 2/06* (2013.01)
*A61F 2/07* (2013.01)
*A61F 2/90* (2013.01)

(52) U.S. Cl.
CPC ... *A61F 2/07* (2013.01); *A61F 2/90* (2013.01); *A61F 2002/061* (2013.01); *A61F 2002/075* (2013.01); *A61F 2250/006* (2013.01); *A61F 2250/0039* (2013.01)

(58) Field of Classification Search
CPC ..................................... A61F 2/07; A61F 2/82
USPC .................................................. 623/1.31–1.36
See application file for complete search history.

(56) References Cited

U.S. PATENT DOCUMENTS 4,180,613 A    12/1979   Vassiliou
4,355,426 A    10/1982   MacGregor (Continued)

FOREIGN PATENT DOCUMENTS

CA    2 497 704     3/2004
CN    2817770 Y     9/2006

(Continued)

OTHER PUBLICATIONS

"E-vita® open plus" product brochure (JOTEC GmbH, Hechingen, Germany), 2010.

(Continued)

*Primary Examiner* — Suzette J Gherbi
(74) *Attorney, Agent, or Firm* — Sughrue Mion, PLLC

(57) ABSTRACT

An endovascular stent-graft system (10) includes fenestrated and crossing stent-grafts (20, 22). The fenestrated stent-graft (20) defines first and second lateral apertures (40, 42) in a central portion (34) thereof, which apertures (40, 42) face in generally radially opposing directions. The crossing stent-graft (22) includes one or more covering elements (58), which at least partially cover both end portions (44, 46) of the crossing stent-graft (22), such that a central portion (54) is at least partially uncovered. Both stent-grafts (20, 22) are sized and shaped such that, when the crossing stent-graft (22) is disposed through both apertures (40, 42) such that the central portion (54) thereof is within the central portion (34) of the fenestrated stent-graft (20), both end portions (44, 46) of the crossing stent-graft (22) (a) pass through both apertures (40, 42), respectively, and (b) when both stent-grafts (20, 22) are in radially-expanded states, form blood-impervious seals with both apertures (40, 42), respectively.

24 Claims, 13 Drawing Sheets

(56) References Cited

U.S. PATENT DOCUMENTS

| | | | |
|---|---|---|---|
| 4,505,767 | A | 3/1985 | Quin |
| 4,562,596 | A | 1/1986 | Kornberg |
| 4,577,631 | A | 3/1986 | Kreamer |
| 4,617,932 | A | 10/1986 | Kornberg |
| 4,665,906 | A | 5/1987 | Jervis |
| 4,739,762 | A | 4/1988 | Palmaz |
| 4,787,899 | A | 11/1988 | Lazarus |
| 4,878,906 | A | 11/1989 | Lindemann et al. |
| 4,886,062 | A | 12/1989 | Wiktor |
| 4,938,740 | A | 7/1990 | Melbin |
| 4,969,458 | A | 11/1990 | Wiktor |
| 5,042,707 | A | 8/1991 | Taheri |
| 5,064,435 | A | 11/1991 | Porter |
| 5,104,404 | A | 4/1992 | Wolff |
| 5,122,136 | A | 6/1992 | Guglielmi et al. |
| 5,133,732 | A | 7/1992 | Wiktor |
| 5,192,286 | A | 3/1993 | Phan et al. |
| 5,234,448 | A | 8/1993 | Wholey et al. |
| 5,425,765 | A * | 6/1995 | Tiefenbrun et al. ........... 606/155 |
| 5,486,183 | A | 1/1996 | Middleman et al. |
| 5,507,769 | A | 4/1996 | Marin et al. |
| 5,509,923 | A | 4/1996 | Middleman et al. |
| 5,522,880 | A | 6/1996 | Barone et al. |
| 5,527,322 | A | 6/1996 | Klein et al. |
| 5,549,662 | A | 8/1996 | Fordenbacher |
| 5,554,181 | A | 9/1996 | Das |
| 5,556,413 | A | 9/1996 | Lam |
| 5,562,724 | A | 10/1996 | Vorwerk et al. |
| 5,607,445 | A | 3/1997 | Summers |
| 5,613,974 | A | 3/1997 | Andreas et al. |
| 5,632,746 | A | 5/1997 | Middleman et al. |
| 5,632,763 | A | 5/1997 | Glastra |
| 5,632,772 | A | 5/1997 | Alcime et al. |
| 5,639,278 | A | 6/1997 | Dereume et al. |
| 5,643,340 | A | 7/1997 | Nunokawa |
| 5,653,743 | A | 8/1997 | Martin |
| 5,676,696 | A | 10/1997 | Marcade |
| 5,676,697 | A | 10/1997 | McDonald |
| 5,728,134 | A | 3/1998 | Barak |
| 5,749,879 | A | 5/1998 | Middleman et al. |
| 5,755,770 | A | 5/1998 | Ravenscroft |
| 5,755,771 | A | 5/1998 | Penn et al. |
| 5,755,777 | A | 5/1998 | Chuter |
| 5,755,781 | A | 5/1998 | Jayaraman |
| 5,769,882 | A | 6/1998 | Fogarty et al. |
| 5,769,884 | A | 6/1998 | Solovay |
| 5,782,903 | A | 7/1998 | Wiktor |
| 5,782,906 | A | 7/1998 | Marshall et al. |
| 5,824,040 | A | 10/1998 | Cox et al. |
| 5,827,321 | A | 10/1998 | Roubin |
| 5,843,170 | A | 12/1998 | Ahn |
| 5,855,600 | A | 1/1999 | Alt |
| 5,860,991 | A | 1/1999 | Klein et al. |
| 5,876,432 | A | 3/1999 | Lau et al. |
| 5,906,641 | A | 5/1999 | Thompson et al. |
| 5,921,994 | A | 7/1999 | Andreas et al. |
| 5,948,018 | A | 9/1999 | Dereume |
| 5,980,552 | A | 11/1999 | Pinchasik |
| 6,015,431 | A | 1/2000 | Thornton et al. |
| 6,016,810 | A | 1/2000 | Ravenscroft |
| 6,030,414 | A | 2/2000 | Taheri |
| 6,033,435 | A | 3/2000 | Penn et al. |
| 6,036,725 | A | 3/2000 | Avellanet |
| 6,059,824 | A | 5/2000 | Taheri |
| 6,099,497 | A | 8/2000 | Adams et al. |
| 6,117,145 | A | 9/2000 | Wood et al. |
| 6,156,064 | A | 12/2000 | Chouinard |
| 6,200,339 | B1 | 3/2001 | Leschinsky et al. |
| 6,206,893 | B1 | 3/2001 | Klein et al. |
| 6,270,524 | B1 | 8/2001 | Kim |
| 6,283,991 | B1 | 9/2001 | Cox et al. |
| 6,290,720 | B1 | 9/2001 | Khosravi et al. |
| 6,312,458 | B1 | 11/2001 | Golds |
| 6,319,287 | B1 | 11/2001 | Frimberger |
| 6,325,823 | B1 | 12/2001 | Horzewski et al. |
| 6,344,056 | B1 | 2/2002 | Dehdashtian |
| 6,395,018 | B1 | 5/2002 | Castaneda |
| 6,406,420 | B1 | 6/2002 | McCarthy |
| 6,428,565 | B1 | 8/2002 | Wisselink |
| 6,506,211 | B1 | 1/2003 | Skubitz et al. |
| 6,613,075 | B1 | 9/2003 | Healy et al. |
| 6,613,078 | B1 | 9/2003 | Barone |
| 6,635,083 | B1 | 10/2003 | Cheng et al. |
| 6,645,242 | B1 | 11/2003 | Quinn |
| 6,648,911 | B1 | 11/2003 | Sirhan |
| 6,652,567 | B1 | 11/2003 | Deaton |
| 6,656,214 | B1 | 12/2003 | Fogarty et al. |
| 6,673,080 | B2 | 1/2004 | Reynolds et al. |
| 6,692,520 | B1 | 2/2004 | Gambale et al. |
| 6,695,833 | B1 | 2/2004 | Frantzen |
| 6,733,523 | B2 | 5/2004 | Shaolian |
| 6,743,195 | B2 | 6/2004 | Zucker |
| 6,752,826 | B2 | 6/2004 | Holloway et al. |
| 6,776,794 | B1 | 8/2004 | Hong et al. |
| 6,814,749 | B2 | 11/2004 | Cox et al. |
| 6,814,752 | B1 | 11/2004 | Chuter |
| 6,824,560 | B2 | 11/2004 | Pelton |
| 6,846,321 | B2 | 1/2005 | Zucker |
| 6,907,285 | B2 | 6/2005 | Denker et al. |
| 6,908,477 | B2 | 6/2005 | McGuckin, Jr. |
| 6,929,660 | B1 | 8/2005 | Ainsworth et al. |
| 6,942,691 | B1 | 9/2005 | Chuter |
| 6,964,679 | B1 | 11/2005 | Marcade et al. |
| 6,986,774 | B2 | 1/2006 | Middleman et al. |
| 7,008,441 | B2 | 3/2006 | Zucker |
| 7,022,131 | B1 | 4/2006 | Derowe et al. |
| 7,044,962 | B2 | 5/2006 | Elliott |
| 7,105,020 | B2 | 9/2006 | Greenberg et al. |
| 7,112,217 | B1 | 9/2006 | Kugler et al. |
| 7,115,127 | B2 | 10/2006 | Lindenbaum et al. |
| 7,144,421 | B2 * | 12/2006 | Carpenter et al. ........... 623/1.31 |
| 7,160,318 | B2 | 1/2007 | Greenberg |
| 7,198,638 | B2 | 4/2007 | Dong |
| 7,201,772 | B2 | 4/2007 | Schwammenthal et al. |
| 7,223,266 | B2 | 5/2007 | Lindenbaum et al. |
| 7,279,003 | B2 | 10/2007 | Berra et al. |
| 7,294,145 | B2 | 11/2007 | Ward |
| 7,306,623 | B2 | 12/2007 | Watson |
| 7,341,598 | B2 | 3/2008 | Davidson et al. |
| 7,407,509 | B2 | 8/2008 | Greenberg et al. |
| 7,425,219 | B2 | 9/2008 | Quadri |
| 7,429,269 | B2 | 9/2008 | Schwammenthal et al. |
| 7,442,204 | B2 | 10/2008 | Schwammenthal et al. |
| 7,473,272 | B2 | 1/2009 | Pryor |
| 7,537,609 | B2 | 5/2009 | Davidson et al. |
| 7,540,881 | B2 | 6/2009 | Meyer et al. |
| 7,544,160 | B2 | 6/2009 | Gross |
| 7,637,939 | B2 | 12/2009 | Tischler |
| 7,645,298 | B2 * | 1/2010 | Hartley et al. ............... 623/1.35 |
| 7,662,161 | B2 | 2/2010 | Briganti et al. |
| 7,662,168 | B2 | 2/2010 | McGuckin, Jr. et al. |
| 7,678,141 | B2 | 3/2010 | Greenan et al. |
| 7,708,704 | B2 | 5/2010 | Mitelberg |
| 7,722,626 | B2 | 5/2010 | Middleman et al. |
| 7,731,732 | B2 | 6/2010 | Ken |
| 7,803,178 | B2 | 9/2010 | Whirley |
| 7,815,673 | B2 | 10/2010 | Bloom et al. |
| 7,887,575 | B2 | 2/2011 | Kujawski |
| 7,955,374 | B2 | 6/2011 | Erickson et al. |
| 7,959,662 | B2 | 6/2011 | Erbel et al. |
| 8,066,755 | B2 | 11/2011 | Zacharias |
| 8,080,053 | B2 | 12/2011 | Satasiya |
| 8,157,810 | B2 | 4/2012 | Case et al. |
| 8,172,892 | B2 | 5/2012 | Chuter |
| 8,221,494 | B2 | 7/2012 | Schreck et al. |
| 8,251,963 | B2 | 8/2012 | Chin et al. |
| 8,292,951 | B2 | 10/2012 | Muzslay |
| 8,353,898 | B2 | 1/2013 | Lutze et al. |
| 2001/0004705 | A1 | 6/2001 | Killion |
| 2001/0014823 | A1 | 8/2001 | Resseman et al. |
| 2001/0034550 | A1 | 10/2001 | Buirge |
| 2001/0037142 | A1 | 11/2001 | Stelter |
| 2001/0044647 | A1 | 11/2001 | Pinchuk et al. |
| 2001/0044651 | A1 | 11/2001 | Steinke |

(56) References Cited

U.S. PATENT DOCUMENTS

| | | |
|---|---|---|
| 2001/0044652 A1 | 11/2001 | Moore |
| 2001/0047198 A1 | 11/2001 | Drasler |
| 2001/0053930 A1 | 12/2001 | Kugler et al. |
| 2002/0040236 A1 | 4/2002 | Lau |
| 2002/0052643 A1 | 5/2002 | Wholey |
| 2002/0052644 A1 | 5/2002 | Shaolian et al. |
| 2002/0072790 A1 | 6/2002 | McGuckin, Jr. |
| 2002/0099441 A1 | 7/2002 | Dehdashtian |
| 2002/0107564 A1 | 8/2002 | Cox |
| 2002/0123791 A1 | 9/2002 | Harrison |
| 2002/0156495 A1 | 10/2002 | Brenneman et al. |
| 2002/0156517 A1 | 10/2002 | Perouse |
| 2002/0198585 A1 | 12/2002 | Wisselink |
| 2003/0033005 A1 | 2/2003 | Houser |
| 2003/0040791 A1 | 2/2003 | Oktay |
| 2003/0074055 A1 | 4/2003 | Haverkost |
| 2003/0093145 A1 | 5/2003 | Lawrence-Brown et al. |
| 2003/0130720 A1 | 7/2003 | DePalma et al. |
| 2003/0153944 A1 | 8/2003 | Phung et al. |
| 2003/0153968 A1 | 8/2003 | Geis et al. |
| 2003/0191523 A1 | 10/2003 | Hojeibane |
| 2003/0199967 A1 | 10/2003 | Hartley et al. |
| 2003/0204236 A1 | 10/2003 | Letort |
| 2003/0204242 A1 | 10/2003 | Zarins et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson |
| 2004/0098091 A1 | 5/2004 | Erbel |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian |
| 2004/0171978 A1 | 9/2004 | Shalaby |
| 2004/0181149 A1 | 9/2004 | Langlotz et al. |
| 2004/0215319 A1 | 10/2004 | Berra et al. |
| 2004/0215327 A1 | 10/2004 | Doig et al. |
| 2004/0260383 A1 | 12/2004 | Stelter |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case |
| 2005/0102018 A1 | 5/2005 | Carpenter et al. |
| 2005/0102021 A1 | 5/2005 | Osborne |
| 2005/0131512 A1 | 6/2005 | Vonderwalde |
| 2005/0131517 A1 | 6/2005 | Hartley et al. |
| 2005/0149166 A1 | 7/2005 | Schaeffer et al. |
| 2005/0154448 A1 | 7/2005 | Cully |
| 2005/0159803 A1 | 7/2005 | Lad |
| 2005/0165480 A1 | 7/2005 | Jordan |
| 2005/0171598 A1 | 8/2005 | Schaeffer et al. |
| 2005/0171599 A1 | 8/2005 | White |
| 2005/0177132 A1 | 8/2005 | Lentz et al. |
| 2005/0177222 A1* | 8/2005 | Mead ............ 623/1.13 |
| 2005/0203606 A1 | 9/2005 | VanCamp |
| 2005/0216018 A1 | 9/2005 | Sennett et al. |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095114 A1 | 5/2006 | Hartley et al. |
| 2006/0100684 A1 | 5/2006 | Elliott |
| 2006/0116748 A1 | 6/2006 | Kaplan |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0281966 A1 | 12/2006 | Peacock, III |
| 2007/0021822 A1 | 1/2007 | Boatman |
| 2007/0043425 A1 | 2/2007 | Hartley et al. |
| 2007/0050011 A1 | 3/2007 | Klein |
| 2007/0055350 A1* | 3/2007 | Erickson et al. ............. 623/1.16 |
| 2007/0055358 A1 | 3/2007 | Krolik et al. |
| 2007/0055360 A1 | 3/2007 | Hanson |
| 2007/0060989 A1 | 3/2007 | Deem et al. |
| 2007/0061002 A1 | 3/2007 | Paul, Jr. |
| 2007/0073373 A1 | 3/2007 | Bonsignore |
| 2007/0088425 A1 | 4/2007 | Schaeffer |
| 2007/0106368 A1* | 5/2007 | Vonderwalde ............... 623/1.13 |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault de la et al. |
| 2007/0156167 A1 | 7/2007 | Connors et al. |
| 2007/0167898 A1 | 7/2007 | Peters et al. |
| 2007/0168018 A1 | 7/2007 | Amplatz |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin |
| 2007/0219610 A1 | 9/2007 | Israel |
| 2007/0219627 A1 | 9/2007 | Chu |
| 2007/0225797 A1 | 9/2007 | Krivoruhko |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0015682 A1 | 1/2008 | Majercak et al. |
| 2008/0058918 A1 | 3/2008 | Watson |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0140178 A1 | 6/2008 | Rasmussen et al. |
| 2008/0147173 A1 | 6/2008 | McIff et al. |
| 2008/0167704 A1 | 7/2008 | Wright et al. |
| 2008/0195191 A1 | 8/2008 | Luo |
| 2008/0249598 A1 | 10/2008 | Sherry |
| 2008/0262595 A1 | 10/2008 | Chu et al. |
| 2008/0262598 A1 | 10/2008 | Elmaleh |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang |
| 2009/0069881 A1 | 3/2009 | Chalekian et al. |
| 2009/0069882 A1 | 3/2009 | Venturelli |
| 2009/0082841 A1 | 3/2009 | Zacharias |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0171437 A1 | 7/2009 | Brocker et al. |

(56) References Cited

U.S. PATENT DOCUMENTS

| | | | |
|---|---|---|---|
| 2009/0227997 A1 | 9/2009 | Wang | |
| 2009/0240316 A1 | 9/2009 | Bruszewski | |
| 2009/0248134 A1 | 10/2009 | Dierking et al. | |
| 2009/0254170 A1 | 10/2009 | Hartley et al. | |
| 2009/0259290 A1 | 10/2009 | Bruszewski et al. | |
| 2009/0287145 A1 | 11/2009 | Cragg et al. | |
| 2010/0004728 A1 | 1/2010 | Rao | |
| 2010/0029608 A1 | 2/2010 | Finley | |
| 2010/0057186 A1 | 3/2010 | West et al. | |
| 2010/0063575 A1 | 3/2010 | Shalev | |
| 2010/0070019 A1 | 3/2010 | Shalev | |
| 2010/0082091 A1 | 4/2010 | Berez | |
| 2010/0161026 A1 | 6/2010 | Brocker et al. | |
| 2010/0161028 A1* | 6/2010 | Chuter et al. | 623/1.13 |
| 2010/0211159 A1 | 8/2010 | Schmid | |
| 2010/0249899 A1* | 9/2010 | Chuter et al. | 623/1.13 |
| 2010/0256725 A1 | 10/2010 | Rasmussen | |
| 2010/0268327 A1* | 10/2010 | Bruszewski et al. | 623/1.18 |
| 2010/0312326 A1* | 12/2010 | Chuter et al. | 623/1.13 |
| 2010/0318171 A1 | 12/2010 | Porter | |
| 2011/0093002 A1 | 4/2011 | Rucker et al. | |
| 2011/0125251 A1 | 5/2011 | Cottone | |
| 2011/0152998 A1 | 6/2011 | Berez | |
| 2011/0208289 A1 | 8/2011 | Shalev | |
| 2011/0208296 A1 | 8/2011 | Duffy et al. | |
| 2011/0208297 A1 | 8/2011 | Tuval et al. | |
| 2011/0208298 A1 | 8/2011 | Tuval et al. | |
| 2011/0218607 A1 | 9/2011 | Arbefeuille et al. | |
| 2011/0264184 A1 | 10/2011 | Heltai | |
| 2011/0288622 A1 | 11/2011 | Chan et al. | |
| 2012/0179236 A1 | 7/2012 | Benary | |
| 2013/0158646 A1 | 6/2013 | Roeder | |
| 2014/0350658 A1* | 11/2014 | Benary et al. | 623/1.15 |
| 2015/0073534 A1* | 3/2015 | Roeder et al. | 623/1.35 |

FOREIGN PATENT DOCUMENTS

| | | |
|---|---|---|
| EP | 1 177 780 | 2/2002 |
| EP | 1 325 716 | 7/2003 |
| EP | 1470797 A2 | 10/2004 |
| EP | 1759666 B1 | 7/2011 |
| JP | 2002-253682 | 9/2002 |
| WO | 98/06355 A1 | 2/1998 |
| WO | 99/34748 A1 | 7/1999 |
| WO | 00/28923 A1 | 5/2000 |
| WO | 03/099108 | 12/2003 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/022495 | 2/2007 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/107885 A2 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/007354 A1 | 1/2011 |
| WO | 2011/055364 | 5/2011 |
| WO | 2011/064782 | 6/2011 |
| WO | 2011/064782 A2 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |

OTHER PUBLICATIONS

Fonseca A et al., "Intravascular ultrasound assessment of the novel AngioSculpt scoring balloon catheter for the treatment of complex coronary lesions," J Invasive Cardiol 20(1):21-7 (Jan. 2008).

Khlif H et al., "Contribution to the Improvement of Textile Vascular Prostheses Crimping," Trends in Applied Sciences Research 6(9):1019-1027 (2011).

An International Search Report dated Feb. 18, 2010, which issued during the prosecution of Applicant's PCT/IL08/000287.

A Written Opinion dated Nov. 12, 2009, which issued during the prosecution of Applicant's PCT/IL08/000287.

An International Search Report dated Apr. 28, 2011, which issued during the prosecution of Applicant's PCT/IB2010/052861.

A Written Opinion dated Dec. 23, 2011, which issued during the prosecution of Applicant's PCT/IB2010/052861.

An International Search Report dated Dec. 3, 2010, which issued during the prosecution of Applicant's PCT/IL2010/000564.

A Written Opinion dated Jan. 14, 2012, which issued during the prosecution of Applicant's PCT/IL2010/000564.

An International Search Report dated Nov. 5, 2010, which issued during the prosecution of Applicant's PCT/IL2010/000549.

A Written Opinion dated Jan. 9, 2012, which issued during the prosecution of Applicant's PCT/IL2010/000549.

An International Search Report dated Oct. 6, 2011, which issued during the prosecution of Applicant's PCT/IL2010/000999.

An International Search Report dated Mar. 10, 2011, which issued during the prosecution of Applicant's PCT/IL2010/000917.

An International Search Report dated Mar. 30, 2011, which issued during the prosecution of Applicant's PCT/IL2010/001018.

An International Search Report dated Jun. 16, 2011, which issued during the prosecution of Applicant's PCT/IL2010/001037.

An International Search Report dated Jul. 7, 2011, which issued during the prosecution of Applicant's PCT/IL2010/001087.

An International Search Report dated Aug. 11, 2011, which issued during the prosecution of Applicant's PCT/IL2011/000135.

An International Search Report dated Mar. 11, 2010, which issued during the prosecution of Applicant's PCT/IL2008/001621.

A Written Opinion dated Jun. 15, 2010, which issued during the prosecution of Applicant's PCT/IL2008/001621.

An International Search Report dated Sep. 3, 2009, which issued during the prosecution of Applicant's PCT/IL2007/001312.

A Written Opinion dated Jul. 31, 2009, which issued during the prosecution of Applicant's PCT/IL2007/001312.

An English translation of an Office Action dated Aug. 25, 2011, which issued during the prosecution of Chinese Patent Application No. 200880014919.9.

An Office Action dated Nov. 12, 2010, which issued during the prosecution of U.S. Appl. No. 12/447,684.

An Office Action dated Apr. 27, 2011, which issued during the prosecution of U.S. Appl. No. 12/447,684.

An Office Action dated Feb. 25, 2013, which issued during the prosecution of U.S. Appl. No. 13/031,871.

An Office Action dated Feb. 27, 2013, which issued during the prosecution of U.S. Appl. No. 12/808,037.

(56) References Cited

OTHER PUBLICATIONS

An Extended European Search Report dated Dec. 13, 2012, which issued during the prosecution of Applicant's European App No. 08719912.1.
An International Search Report together with Written Opinion both dated Sep. 6, 2012, which issued during the prosecution of Applicant's PCT/IL2012/000190.
An International Search Report together with Written Opinion both dated Aug. 31, 2012, which issued during the prosecution of Applicant's PCT/IL2012/000148.
An Office Action dated Oct. 11, 2012, which issued during the prosecution of U.S. Appl. No. 13/031,871.
An Office Action dated Jun. 19, 2012, which issued during the prosecution of U.S. Appl. No. 12/808,037.
An International Search Report together with Written Opinion both dated Sep. 24, 2012, which issued during the prosecution of Applicant's PCT/IL2012/000060.
An International Search Report together with Written Opinion both dated Oct. 1, 2012, which issued during the prosecution of Applicant's PCT/IL2012/000241.
An International Search Report together with Written Opinion both dated Oct. 4, 2012, which issued during the prosecution of Applicant's PCT/IL2012/000269.
An International Search Report together with Written Opinion both dated Nov. 27, 2012, which issued during the prosecution of Applicant's PCT/IL2012/000300.
An Office Action dated Mar. 24, 2011, which issued during the prosecution of U.S. Appl. No. 12/529,936.
An Office Action dated Oct. 28, 2011, which issued during the prosecution of U.S. Appl. No. 12/529,936.
An International Search Report together with Written Opinion both dated Jun. 14, 2013, which issued during the prosecution of Applicant's PCT/IL2012/050506.
U.S. Appl. No. 61/219,758, filed Jun. 23, 2009.
U.S. Appl. No. 61/221,074, filed Jun. 28, 2009.
Fattori et al., Degenerative aneurysm of the descending aorta. Endovascular Treatment. pp. 1-11, 2007, European Association for Cardio-Thoracic Surgery.
Van Prehn J et al., "Oversizing of aortic stent grafts for abdominal aneurysm repair: a systematic review of the benefits and risks," Eur J Vasc Endovasc Surg. Jul. 2009;38(1):42-53. Epub May 9, 2009 (abstract only).
An International Search Report dated May 23, 2011, which issued during the prosecution of Applicant's PCT/IL2010/001087.
An International Search Report dated Jun. 9, 2011, which issued during the prosecution of Applicant's PCT/IL2010/001018.
Advisory Action, dated Feb. 13, 2014, issued by the United States Patent and Trademark Office, in counterpart U.S. Appl. No. 13/807,880.
Office Action, dated Feb. 28, 2014, issued by the United States Patent and Trademark Office, in counterpart U.S. Appl. No. 13/512,778.
Office Action, dated Mar. 28, 2014, issued by the United States Patent and Trademark Office, in counterpart U.S. Appl. No. 13/519,971.
Office Action, dated Jan. 28, 2014, issued by the State Intellectual Property Office of the People's Republic of China, in counterpart Application No. 201080036970.7.
Office Action, dated Apr. 10, 2014, issued by the United States Patent and Trademark Office, in counterpart U.S. Appl. No. 13/807,906.
Office Action, dated Apr. 24, 2014, issued by the United States Patent and Trademark Office, in counterpart U.S. Appl. No. 13/380,278.
Office Action, dated Apr. 28, 2014, issued by the United States Patent and Trademark Office, in counterpart U.S. Appl. No. 13/939,798.
Extended European Search Report, dated Feb. 24, 2014, issued by the European Patent Office, in counterpart Application No. 12803376.8.
Communication dated Oct. 8, 2014, issued by the State Intellectual Property Office of the People's Republic of China in counterpart Application No. 201080036970.7.
Non-final Office Action dated Feb. 5, 2015 in U.S. Appl. No. 13/384,075.
European Search Report dated Feb. 26, 2015 in EP Application No. 12806964.8.
International Search Report and Written Opinion dated Mar. 18, 2015 in PCT/IL2014/050973.
English Translation of Office Action dated Mar. 19, 2015 in Chinese Application No. 201080036970.7.
European Search Report dated Mar. 20, 2015 in EP Application No. 08861980.4.
Restriction Requirement dated Feb. 23, 2015 in U.S. Appl. No. 13/513,397.
Non-final Office Action dated Apr. 14, 2015 in U.S. Appl. No. 14/130,213.
European Search Report dated Apr. 22, 2015 in EP Application No. 12828495.7.

* cited by examiner

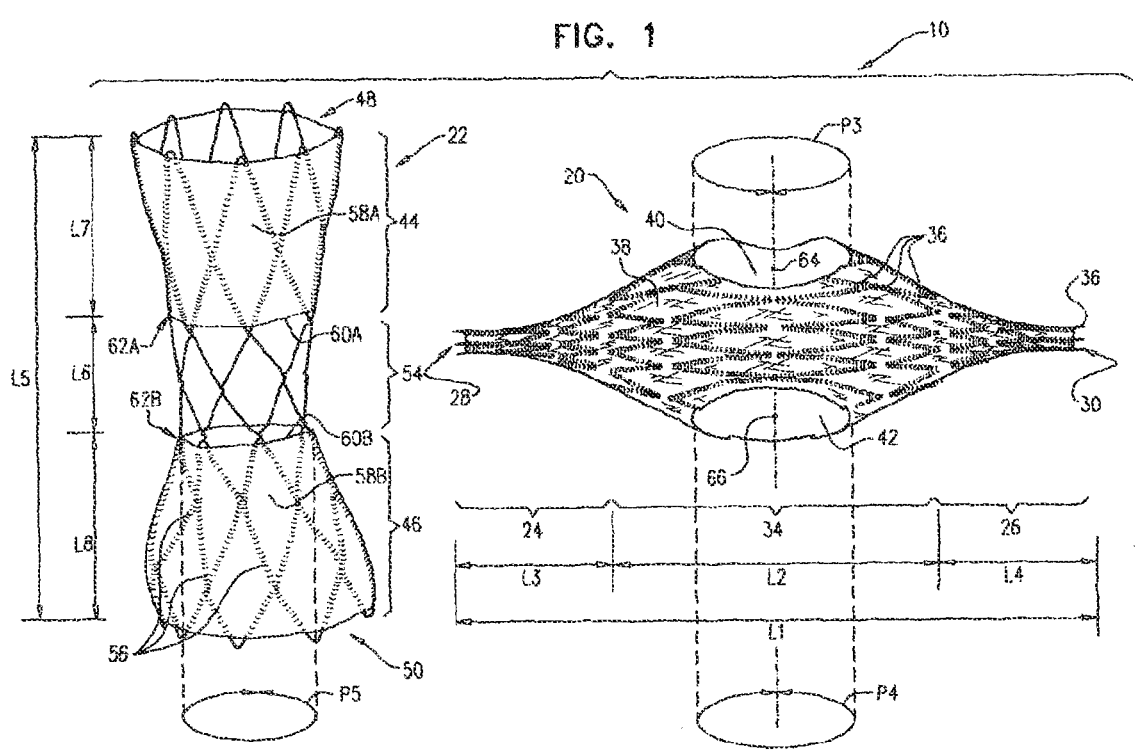

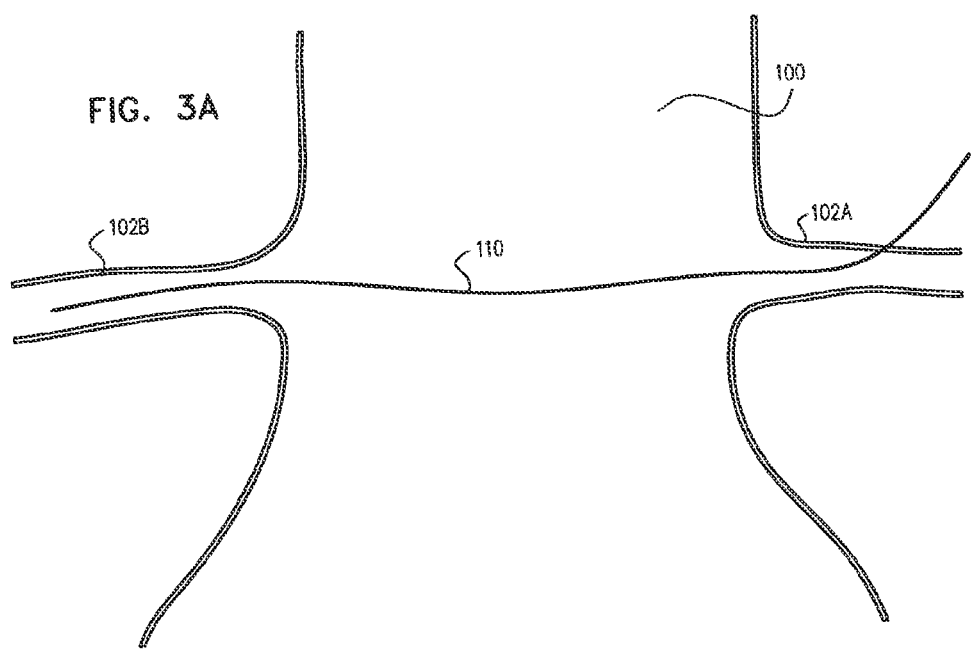

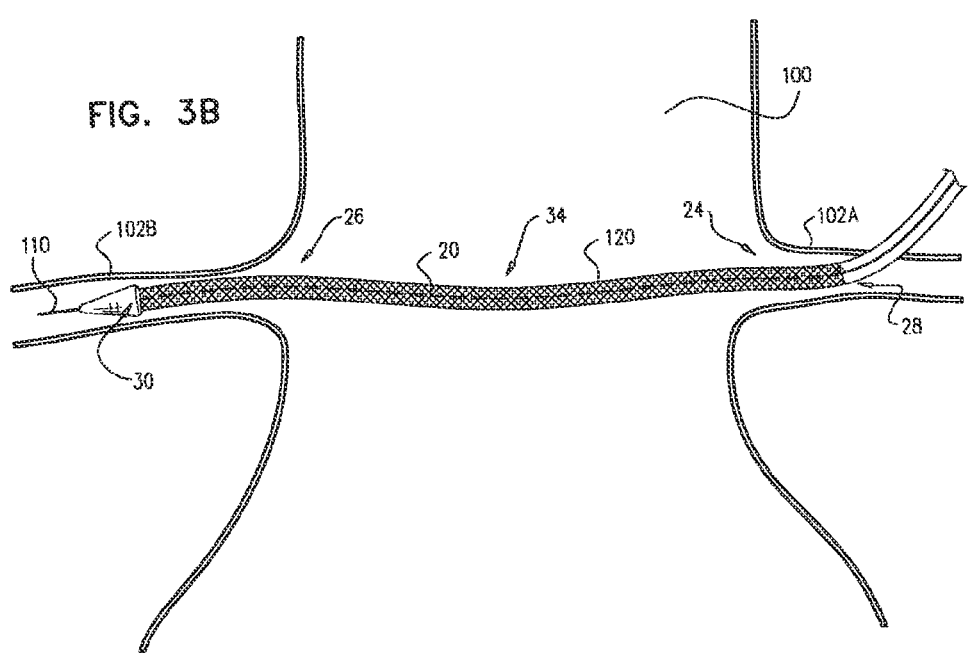

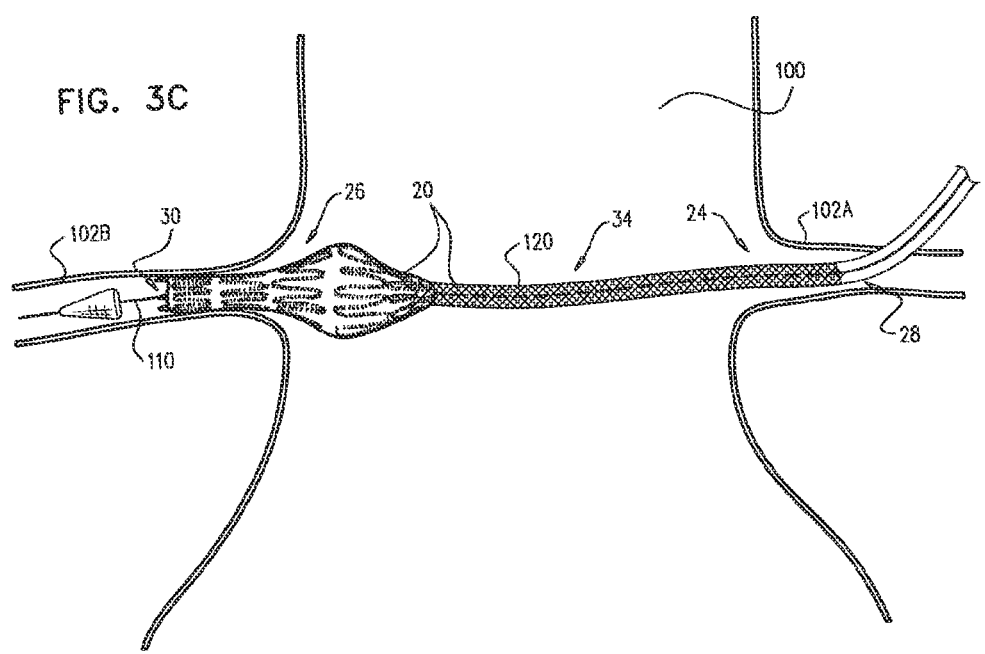

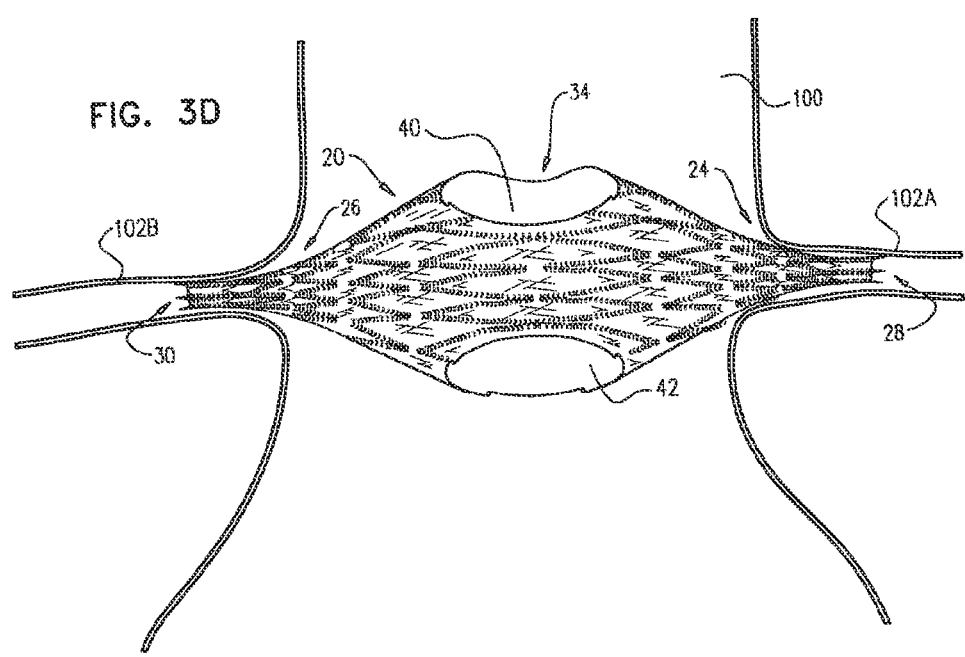

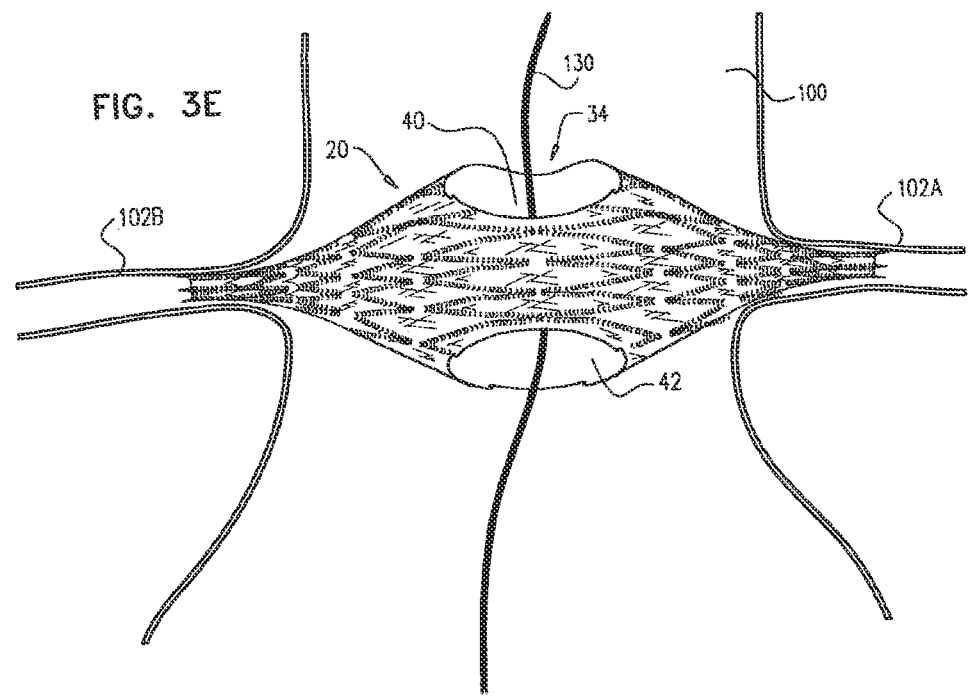

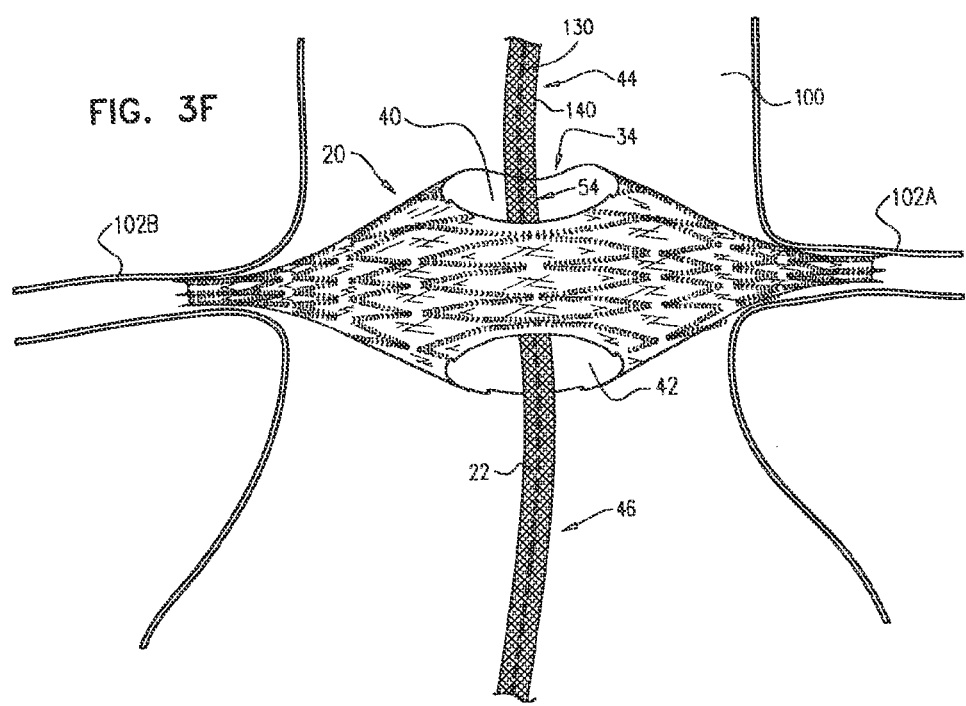

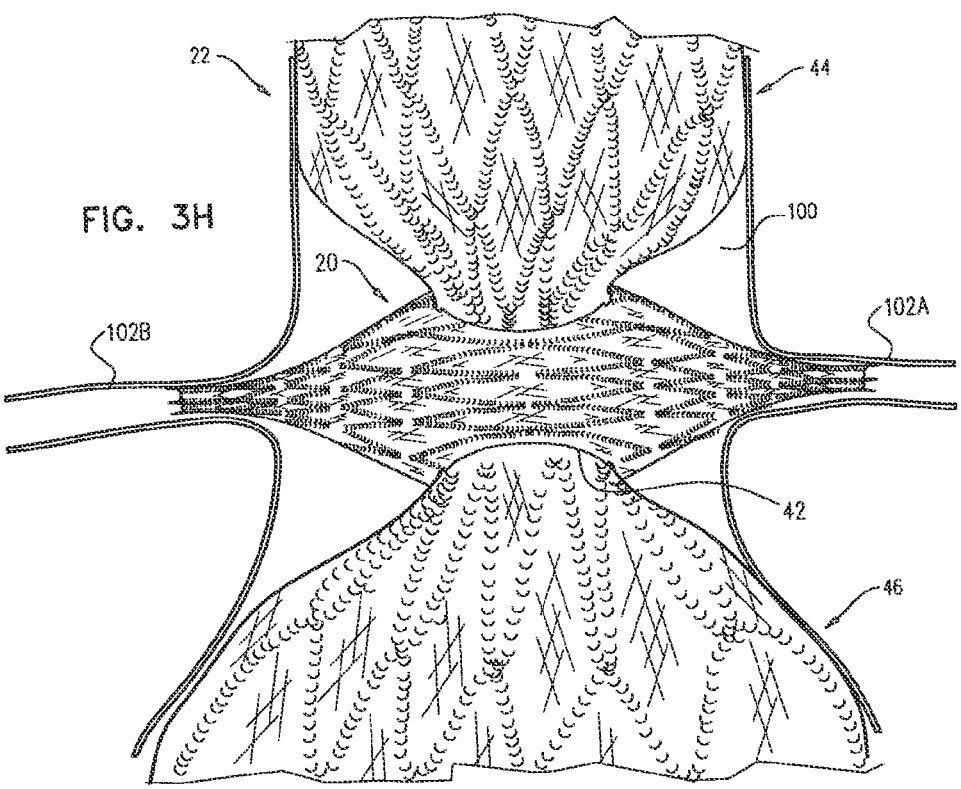

ENDOVASCULAR STENT-GRAFT SYSTEM WITH FENESTRATED AND CROSSING STENT-GRAFTS

CROSS REFERENCE TO RELATED APPLICATIONS

This application is a National Stage of International Application No. PCT/IL2010/001037, filed on Dec. 8, 2010, which claims priority from U.S. Provisional Application No. 60/267,453, filed on Dec. 8, 2009, the contents of all of which are incorporated herein by reference in their entirety.

FIELD OF THE APPLICATION

This present application relates generally to prostheses and surgical methods, and specifically to tubular prostheses, including endovascular grafts and stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms.

PCT Publication WO 2008/107885 to Shalev et al., and US Patent Application Publication 2010/0063575 to Shalev et al. in the US national stage thereof, which are incorporated herein by reference, describe a multiple-component expandable endoluminal system for treating a lesion at a bifurcation, including a self expandable tubular root member having a side-looking engagement aperture, and a self expandable tubular trunk member comprising a substantially blood impervious polymeric liner secured therealong. Both have a radially-compressed state adapted for percutaneous intraluminal delivery and a radially-expanded state adapted for endoluminal support.

The following references may be of interest:
U.S. Pat. No. 4,938,740
U.S. Pat. No. 5,824,040 to Cox et al.
U.S. Pat. No. 7,044,962 to Elliott
US Patent Application Publication 2006/0229709 to Morris et al.
US Patent Application Publication 2006/0241740 to Vardi et al.
US Patent Application Publication 2008/0109066 to Quinn

SUMMARY OF APPLICATIONS

Some applications of the present invention provide a multi-component stent-graft system comprising a fenestrated stent-graft and a crossing stent-graft. A central portion of the fenestrated stent-graft is shaped so as to define first and second lateral apertures that face in generally radially opposing directions. A central portion of the crossing stent-graft is at least partially not covered by covering elements of the crossing stent-graft, so as to allow blood flow through the central portion. When the multi-component stent-graft system is assembled, the crossing stent-graft passes through the apertures and the central portion of the fenestrated stent-graft, so as to form blood-impervious seals with the apertures, and allow blood flow through and between the fenestrated and crossing stent-grafts.

For some applications, the fenestrated stent-graft is deployed such that first and second end portions thereof are at least partially positioned in respective first and second branching blood vessels of a main blood vessel of a patient, and the central portion of the stent-graft is positioned in the main blood vessel. After the fenestrated stent-graft assumes a radially-expanded state, the crossing stent-graft is introduced into the main blood vessel, and, while in a radially-compressed state, is passed through the second and the first apertures, such that the central portion of the crossing stent-graft is within the central portion of the fenestrated stent-graft, and the first and the second end portions of the crossing stent-graft pass through the first and the second apertures, respectively.

The crossing stent-graft is transitioned to its radially-expanded state, such that first and second end portions thereof form blood-impervious seals with the first and the second apertures, respectively. As a result, interior spaces defined by all of the following are in fluid communication with one another: the first and the second end portions and the central portion of the fenestrated stent-graft, and the first and the second end portions and the central portion of the crossing stent-graft.

For some applications, the main blood vessel is a descending abdominal aorta, and the branching blood vessels are the left and right renal arteries. For some applications, the stent-graft system is used for treating an abdominal aortic aneurysm, such as a sub-renal aortic aneurysm.

For applications in which the ends of the fenestrated stent-graft are positioned in the left and right renal arteries, the fenestrated stent-graft is typically deployed prior to introducing the crossing stent-graft. There is thus no need to position the fenestrated stent-graft with respect to the crossing stent-graft while deploying the fenestrated stent-graft. Therefore, the ends of the fenestrated stent-graft are readily positioned properly in the renal arteries, even though the renal arteries generally branch from the aorta at different respective axial positions along the aorta. The crossing stent-graft is also readily passed through the apertures of the fenestrated stent-graft. In contrast, when deploying some aortic stent-grafts that comprise branching tubular structures, it is sometimes difficult to insert these tubular structures into the renal arteries, particularly since the renal arteries having differing axial positions in different patients. In addition, it could be necessary to use a plurality of guidewires, which would increase the crossing profile of the deployment tool.

There is therefore provided, in accordance with an application of the present invention, apparatus including an endovascular stent-graft system, which includes:

a fenestrated stent-graft, which includes first and second end portions and a central portion disposed longitudinally therebetween, and which includes a fenestrated support structure and a fenestrated covering element, which is securely attached to and covers at least a portion of the fenestrated support structure, wherein the fenestrated support structure and the fenestrated covering element are shaped so as to together define first and second lateral apertures in the central portion, which apertures face in generally radially opposing directions, when the fenestrated stent-graft is in a radially-expanded state thereof; and a crossing stent-graft, which includes first and second end portions and a central portion disposed longitudinally therebetween, and which includes a crossing support structure and one or more crossing covering elements, which are securely attached to and at least partially cover the first and the second end portions, such that the central portion is at least partially uncovered when the crossing stent-graft is in a radially-expanded state thereof, wherein the fenestrated and the crossing stent-grafts are sized and shaped such that, when the crossing stent-graft is disposed through the first and the second apertures such that the central portion of the crossing stent-graft is within the central portion of the fenestrated stent-graft, the first and the second end portions of the crossing stent-graft (a) pass through the first and the second apertures, respectively, and (b) when the fenestrated and the crossing stent-grafts are in their radially-expanded states, form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft.

For some applications, the central portion of crossing stent-graft is generally sized to fit a perimeter of each of the apertures, when the stent-grafts are unconstrained in their radially-expanded states.

For some applications, the one or more crossing covering elements include first and second covering elements, which are securely attached to and at least partially cover the first and the second end portions of the crossing stent-graft, respectively.

For some applications, when the crossing stent-graft is unconstrained in its radially-expanded state: one end of the first covering element defines a generally elliptical circumferential junction between the first end portion and the central portion of the crossing stent-graft, one end of the second covering element defines a generally elliptical circumferential junction between the second end portion and the central portion of the crossing stent-graft, and the central portion of the crossing stent-graft is entirely uncovered. For some applications, a perimeter of the central portion of the crossing stent-graft varies by less than 30% therealong, when the crossing stent-graft is unconstrained in its radially-expanded state. For some applications, a longitudinal length of the central portion of the crossing stent-graft is between 25% and 120% of a distance between the apertures, when the crossing stent-graft is unconstrained in its radially-expanded state.

For some applications, the central portion of the fenestrated stent-graft is generally fusiform, when the fenestrated stent-graft is unconstrained in its radially-expanded state. For some applications, the fenestrated stent-graft is generally fusiform, when the fenestrated stent-graft is unconstrained in its radially-expanded state.

For some applications, a perimeter of the central portion of the crossing stent-graft varies by less than 50% therealong, when the crossing stent-graft is unconstrained in its radially-expanded state.

For some applications, one or both of the apertures are generally elliptical, when the fenestrated stent-graft is unconstrained in its radially-expanded state.

For some applications, respective centers of the apertures are positioned less than a distance from a longitudinal midpoint of the fenestrated stent-graft, which distance is measured along a longitudinal axis of the fenestrated stent-graft and equals 40% of a longitudinal length of the fenestrated stent-graft, when the fenestrated stent-graft is unconstrained in its radially-expanded state.

For some applications, the first and the second end portions of the fenestrated stent-graft have respective ends that coincide with respective ends of the fenestrated stent-graft, and each of the ends of the first and the second end portions has a perimeter of between 10 and 100 mm, when the fenestrated stent-graft is unconstrained in its radially-expanded state.

For some applications, a greatest perimeter of the central portion of the fenestrated stent-graft is between 6 and 16 cm, when the fenestrated stent-graft is unconstrained in its radially-expanded state.

For some applications, the first and the second end portions of the crossing stent-graft have respective medial ends, at which the first and the second end portions are joined to the central portion of the crossing stent-graft, respectively, and at least one of the first and the second end portions of the crossing stent-graft is outwardly flared toward the central portion of the crossing stent-graft, when the crossing stent-graft is in its radially-expanded state.

For some applications, the first and the second end portions of the fenestrated stent-graft have respective ends that coincide with respective ends of the fenestrated stent-graft, and a ratio of (a) a greatest perimeter of the central portion of the fenestrated stent-graft to (b) a perimeter of each of the ends of the first and the second end portions of the fenestrated stent-graft is between 4 and 15, when the fenestrated stent-graft is unconstrained in its radially-expanded state.

For some applications, a perimeter of the first end portion of the crossing stent-graft varies by less than 20% along a length thereof, when the crossing stent is unconstrained in its radially-expanded state. For some applications, a perimeter of the second end portion of the crossing stent-graft varies by less than 20% along a length thereof, when the crossing stent-graft is unconstrained in its radially-expanded state.

For some applications, the fenestrated covering element does not extend to at least one end of the fenestrated stent-graft, such that the fenestrated support structure is not covered near the end. For some applications, the one or more crossing covering elements do not extend to at least one end of the crossing stent-graft, such that the crossing support structure is not covered near the end.

For some applications, an average perimeter of the central portion of the crossing stent-graft (a) is less than an average perimeter of the first end portion of the crossing stent-graft and (b) is less than an average perimeter of the second end portion of the crossing stent-graft, when the crossing stent-graft is unconstrained in its radially-expanded state.

For some applications, a greatest perimeter of at least one of the first end portion and the second end portion of the crossing stent-graft is between 6 and 13 cm, when the crossing stent-graft is unconstrained in its radially-expanded state. For some applications, a greatest perimeter of the central portion of the crossing stent-graft is between 1.5 and 10 cm, when the crossing stent-graft is unconstrained in its radially-expanded state.

For any of the applications described above, each of the crossing support structure and the fenestrated support structure may include a metal. For some applications, the metal is selected from the group consisting of: a super-elastic metal, and a shape memory alloy. For some applications, the metal includes Nitinol.

For any of the applications described above, the fenestrated and the crossing stent-grafts may be self-expanding.

For any of the applications described above, the crossing stent-graft, when in its radially-expanded state, may have an hour-glass shape, and the central portion of the crossing stent-graft may be shaped so as to define a stricture in the hour-glass shape.

For any of the applications described above, the crossing stent-graft may be configured to be implanted in a main blood vessel having an aneurysm, and the first and the second end portions of the fenestrated stent-graft may be configured to be implanted at least partially in respective branching blood vessels of the main blood vessel, such that the central portion of the fenestrated stent-graft is positioned in the main blood vessel.

For any of the applications described above, the fenestrated stent-graft may be configured to be implanted in a main blood vessel having an aneurysm, and the first and the second end portions of the crossing stent-graft may be configured to be implanted at least partially in respective branching blood vessels of the main blood vessel, such that the central portion of the crossing stent-graft is positioned in the main blood vessel.

For any of the applications described above, the apparatus may further include:

a first delivery shaft, and the fenestrated stent-graft is initially placed in the first delivery shaft in a radially-compressed state of the fenestrated stent-graft, and the fenestrated stent-graft is configured to transition to its radially-expanded state upon being deployed from the first delivery shaft; and a second delivery shaft, and the crossing stent-graft is initially placed in the second delivery shaft in a radially-compressed state of the crossing stent-graft, and the crossing stent-graft is configured to transition to its radially-expanded state upon being deployed from the second delivery shaft.

There is further provided, in accordance with an application of the present invention, a method for treating a patient, the method including:

providing (a) a fenestrated stent-graft, which includes first and second end portions and a central portion disposed longitudinally therebetween, which central portion is shaped so as to define first and second lateral apertures that face in generally radially opposing directions, when the fenestrated stent-graft is in a radially-expanded state thereof, and (b) a crossing stent-graft, which includes first and second end portions and a central portion disposed longitudinally therebetween, and which includes a crossing support structure and one or more crossing covering elements, which are securely attached to and at least partially cover the first and the second end portions, such that the central portion is at least partially uncovered when the crossing stent-graft is in a radially-expanded state thereof;

deploying the fenestrated stent-graft such that the first and the second end portions thereof are at least partially positioned in respective first and second branching blood vessels of a main blood vessel of the patient, the central portion of the fenestrated stent-graft is positioned in the main blood vessel, and the fenestrated stent-graft is in its radially-expanded state;

thereafter, introducing the crossing stent-graft into the main blood vessel, and passing the crossing stent-graft, while in a radially-compressed state thereof, through the second and the first apertures, such that the central portion of the crossing stent-graft is within the central portion of the fenestrated stent-graft, and the first and the second end portions of the crossing stent-graft pass through the first and the second apertures, respectively; and transitioning the crossing stent-graft to its radially-expanded state, such that the first and the second end portions of the crossing stent-graft form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft.

For some applications, deploying the fenestrated stent-graft includes laparoscopically introducing the fenestrated stent-graft into the first branching blood vessel, and advancing the fenestrated stent-graft across the main blood vessel to the second branching blood vessel. Alternatively or additionally, for some applications, introducing the crossing stent-graft includes endovascularly introducing the crossing stent-graft into the main blood vessel.

For some applications, the method further includes identifying that the patient suffers from an aneurysm of the main blood vessel, and introducing the crossing stent-graft includes introducing the crossing stent-graft responsively to the identifying.

For some applications, providing the fenestrated stent-graft includes providing the fenestrated stent-graft in which the central portion thereof is generally fusiform, when the fenestrated stent-graft is unconstrained in its radially-expanded state. For some applications, providing the fenestrated stent-graft includes providing the fenestrated stent-graft which is generally fusiform, when the fenestrated stent-graft is unconstrained in its radially-expanded state.

There is still further provided, in accordance with an application of the present invention, a method for treating a patient, the method including:

providing (a) a fenestrated stent-graft, which includes first and second end portions and a central portion disposed longitudinally therebetween, which central portion is shaped so as to define first and second lateral apertures that face in generally radially opposing directions, when the fenestrated stent-graft is in a radially-expanded state thereof, and (b) a crossing stent-graft, which includes first and second end portions and a central portion disposed longitudinally therebetween, and which includes a crossing support structure and one or more crossing covering elements, which are securely attached to and at least partially cover the first and the second end portions, such that the central portion is at least partially uncovered when the crossing stent-graft is in a radially-expanded state thereof;

deploying the fenestrated stent-graft in a main blood vessel of the patient such that the first and the second apertures generally face first and second branching blood vessels of the main blood vessel, and the fenestrated stent-graft is in its radially-expanded state;

thereafter, introducing the crossing stent-graft into the first branching blood vessel, and passing the crossing stent-graft, while in a radially-compressed state thereof, through the first and the second apertures, and into the second branching blood vessel, such that the central portion of the crossing stent-graft is within the central portion of the fenestrated stent-graft, and the first and the second end portions of the crossing stent-graft pass through the first and the second apertures, respectively; and transitioning the crossing stent-graft to its radially-expanded state, such that the first and the second end portions of the crossing stent-graft form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft.

For some applications, deploying the fenestrated stent-graft includes endovascularly introducing the crossing stent-graft into the main blood vessel. Alternatively or additionally, for some applications, introducing the crossing stent-graft includes laparoscopically introducing the crossing stent-graft into the first branching blood vessel, and advancing the crossing stent-graft across the main blood vessel to the second branching blood vessel.

For some applications, the method further includes identifying that the patient suffers from an aneurysm of the main blood vessel, and deploying the fenestrated stent-graft includes deploying the fenestrated stent-graft responsively to the identifying.

For some applications of either of the methods described above, the main blood vessel is an artery, such as a descending abdominal aorta. For some applications, one of the first and the second branching blood vessels is a left renal artery, and another of the first and the second branching blood vessels is a right renal artery.

For some applications of either of the methods described above:

deploying the fenestrated stent-graft includes introducing the fenestrated stent-graft while placed in a first delivery shaft in a radially-compressed state of the fenestrated stent-graft, and transitioning the fenestrated stent-graft to its radially-expanded state upon deploying the fenestrated stent-graft from the first delivery shaft, and introducing the crossing stent-graft includes introducing the crossing stent-graft while placed in a second delivery shaft in a radially-compressed state of the crossing stent-graft, and transitioning the crossing stent-graft includes transitioning the crossing stent-graft to its radially-expanded state upon deploying the crossing stent-graft from the second delivery shaft.

For some applications of either of the methods described above, providing the crossing stent-graft includes providing the crossing stent-graft in which the central portion thereof is generally sized to fit a perimeter of each of the apertures, when the stent-grafts are unconstrained in their radially-expanded states.

For some applications of either of the methods described above, providing the crossing stent-graft includes providing the crossing stent-graft in which the one or more crossing covering elements include first and second covering elements, which are securely attached to and at least partially cover the first and the second end portions of the crossing stent-graft, respectively. For some applications, providing the crossing stent-graft includes providing the crossing stent-graft in which, when the crossing stent-graft is unconstrained in its radially-expanded state: one end of the first covering element defines a generally elliptical circumferential junction between the first end portion and the central portion of the crossing stent-graft, one end of the second covering element defines a generally elliptical circumferential junction between the second end portion and the central portion of the crossing stent-graft, and the central portion of the crossing stent-graft is entirely uncovered. For some applications, providing the crossing stent-graft includes providing the crossing stent-graft in which a perimeter of the central portion of the crossing stent-graft varies by less than 30% therealong, when the crossing stent-graft is unconstrained in its radially-expanded state.

For some applications of either of the methods described above, providing the fenestrated stent-graft includes providing the fenestrated stent-graft in which one or both of the apertures are generally elliptical, when the fenestrated stent-graft is unconstrained in its radially-expanded state.

The present invention will be more fully understood from the following detailed description of embodiments thereof, taken together with the drawings, in which:

BRIEF DESCRIPTION OF THE DRAWINGS

FIGS. 1 and 2A-B are schematic illustrations of a multi-component stent-graft system in disassembled and assembled states, respectively, in accordance with an application of the present invention;

FIGS. 3A-H are schematic illustrations of an exemplary transluminal delivery procedure for implanting the multi-component stent-graft system of FIGS. 1 and 2A-B, in accordance with an application of the present invention;

DETAILED DESCRIPTION OF APPLICATIONS

Figure 2A:
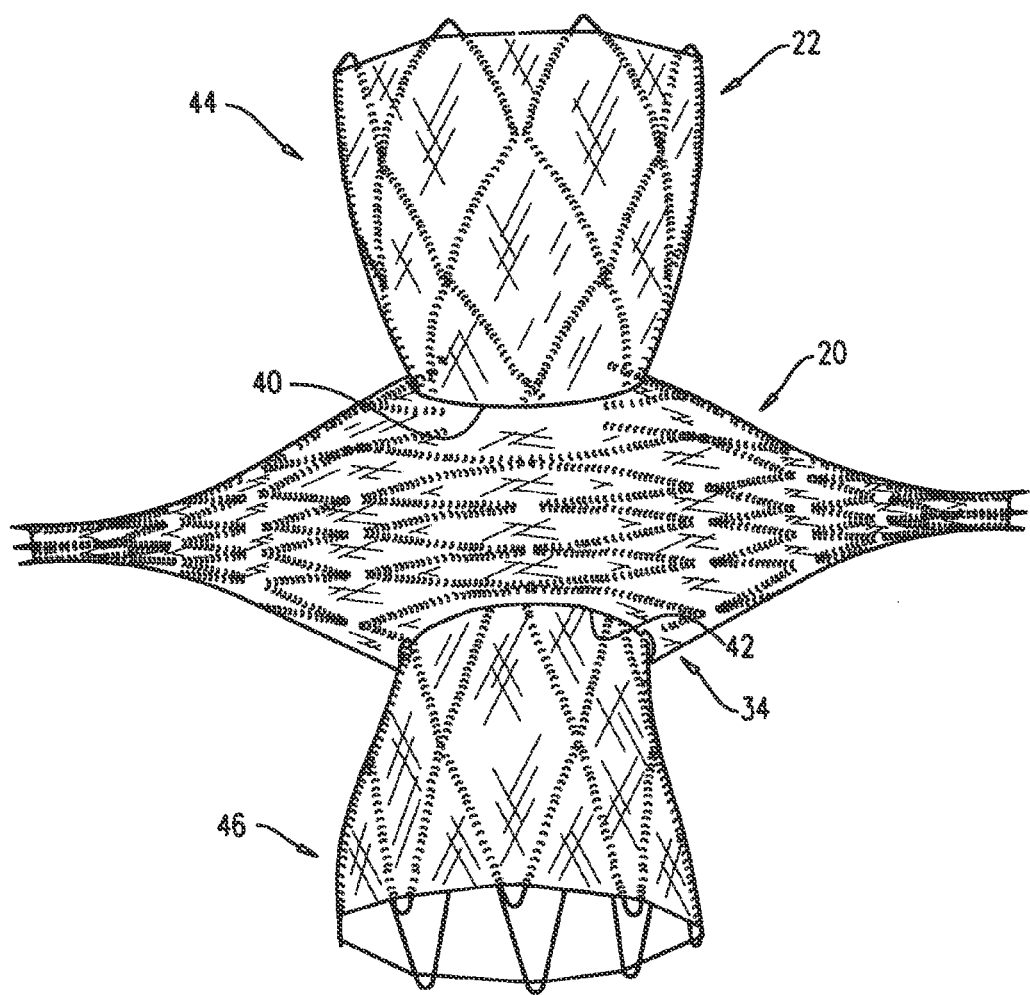
Figure 2B:
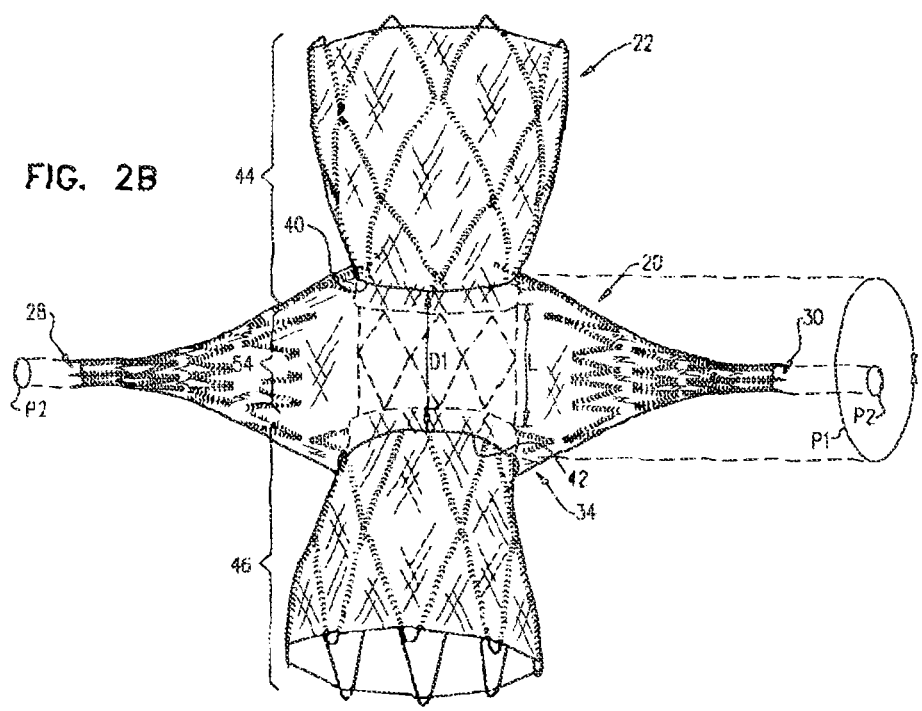

FIGS. 1 and 2A-B are schematic illustrations of a multi-component stent-graft system 10 in disassembled and assembled states, respectively, in accordance with an application of the present invention. Multi-component stent-graft system 10 comprises a fenestrated stent-graft 20 and a crossing stent-graft 22. The stent-grafts are configured to assume radially-compressed states, such as when initially positioned in one or more delivery shafts of one or more delivery tools, such as described hereinbelow with reference to FIGS. 3B and 3F, and to assume radially-expanded states upon being deployed from the delivery shafts, such as described hereinbelow with reference to FIGS. 3C-D and 3G-H. For some applications, the stent-grafts are relaxed in their radially-expanded states. For some applications, the stent-grafts are configured to be self-expanding. For example, they may be heat-set to assume the radially-expanded states.

FIG. 1 shows stent-graft system 10 in a disassembled state, with both stent-grafts in their radially-expanded states. FIGS. 2A-B shows the stent-graft system in an assembled state, with both stent-grafts in their radially-expanded states. When the stent-graft is assembled, crossing stent-graft 22 passes through fenestrated stent-graft 20, and is coupled thereto so as to form blood-impervious seals, as described in more detail hereinbelow.

As shown in FIG. 1, fenestrated stent-graft 20 includes (a) first and second end portions 24 and 26, which extend to respective ends 28 and 30 of stent-graft 20, and (b) a central portion 34 disposed longitudinally between end portions 24 and 26. Fenestrated stent-graft 20 comprises a fenestrated support structure 36 and a fenestrated covering element 38, which is securely attached to and covers at least a portion of the fenestrated support structure. Fenestrated support structure 36 and fenestrated covering element 38 are shaped so as to together define first and second lateral apertures 40 and 42 in central portion 34, which apertures face in generally radially opposing directions, when the fenestrated stent-graft is in its radially-expanded state. Typically, one or both of apertures 40 and 42 are generally elliptical, when the fenestrated stent-graft is in its radially-expanded state.

Fenestrated support structure 36 typically comprises a plurality of structural stent elements. For some applications, at least some of, e.g., all of, the structural stent elements are interconnected (as shown in the figures), while for other applications, at least a portion of, e.g., all, of the structural stent elements are not interconnected (configuration not shown). For some applications, support structure 36 comprises a metal, such as a super-elastic alloy and/or a shape memory allow, e.g., Nitinol. For some applications, one or both of apertures 40 and 42 are circumscribed by respective generally annular structural stent elements of the support element.

Covering element 38 serves as a blood flow guide through at least a portion of fenestrated stent-graft 20. Covering element 38 (and covering element(s) 58 of crossing stent-graft 22, described hereinbelow) typically comprises at least one biologically-compatible substantially blood-impervious flexible sheet, which is attached (such as by stitching) to at least a portion of the support structure, on either side of the surface defined by the support structure. The flexible sheet may comprise, for example, a polymeric material (e.g., a polyester, or polytetrafluoroethylene), a textile material (e.g., polyethylene terephthalate (PET)), natural tissue (e.g., saphenous vein or collagen), or a combination thereof.

For some applications, covering element 38 does not extend to at least one of ends 28 and 30 of fenestrated stent-graft 20, such that support structure 36 is not covered near the end. For some applications, this uncovered portion is flared, when the fenestrated stent-graft is in its radially-expanded state. The uncovered portion may facilitate proper fixation and sealing of the stent-graft with the blood vessel wall.

For some applications, as shown in FIGS. 1 and 2A-B, central portion 34 of fenestrated stent-graft 20, and/or the entirety of fenestrated stent-graft 20, is generally fusiform, when the fenestrated stent-graft is in its radially-expanded state.

For some applications, each of ends 28 and 30 of fenestrated stent-graft 20 has a perimeter of at least 10 mm, no more than 100 mm, and/or between 10 and 100 mm, such as of at least 8 mm, no more than 14 mm, and/or between 8 and 14 mm, when the fenestrated stent-graft is unconstrained in its radially-expanded state, i.e., no forces are applied to the stent-graft by a delivery tool, walls of a blood vessel, or otherwise. For some applications, fenestrated stent-graft 20, when unconstrained in its radially-expanded state, has a total length L1 of at least 3 cm, no more than 20 cm, and/or between 3 and 20 cm. For some applications, central portion 34 has a length L2 of at least 1 cm, no more than 10 cm, and/or between 1 and 10 cm, when stent-graft 20 is unconstrained in its radially-expanded state. For some applications, first and second end portions 24 and 26 have respective lengths L3 and L4, each of which is at least 1 cm, no more than 10 cm, and/or between 1 and 10 cm, when stent-graft 20 is unconstrained in its radially-expanded state.

For some applications, a greatest perimeter P1 (labeled in FIG. 2B) of central portion 34 is at least 6 cm, no more than 16 cm, and/or between 6 and 16 cm, when fenestrated stent-graft 20 is unconstrained in its radially-expanded state.

For some applications, a ratio of (a) greatest perimeter P1 of central portion 34 of fenestrated stent-graft 20 to (b) a perimeter P2 (labeled in FIG. 2B) of each of ends 28 and 30 of first and second end portions 24 and 26 of fenestrated stent-graft 20 is at least 4, no more than 15, and/or between 4 and 15, when the fenestrated stent-graft is unconstrained in its radially-expanded state.

For some applications, first aperture 40 has a perimeter P3 of at least 3 cm, no more than 12 cm, and/or between 3 and 12 cm, when the fenestrated stent-graft is unconstrained in its radially-expanded state. For some applications, second aperture 42 has a perimeter P4 of at least 3 cm, no more than 12 cm, and/or between 3 and 12 cm, when the fenestrated stent-graft is unconstrained in its radially-expanded state. For some applications, perimeters P3 and P4 are generally equal, such as within 10% of each other, when the fenestrated stent-graft is unconstrained in its radially-expanded state.

For some applications, respective centers 64 and 66 of apertures 40 and 42 are positioned less than a distance from a longitudinal midpoint 68 the fenestrated stent-graft 20, which distance is measured along a longitudinal axis of the fenestrated stent-graft and equals 40% of longitudinal length L1 of fenestrated stent-graft 20, such as 10%, when the fenestrated stent-graft is unconstrained in its radially-expanded state.

Also as shown in FIG. 1, crossing stent-graft 22 includes (a) first and second end portions 44 and 46, which extend to respective ends 48 and 50 of stent-graft 22, and (b) a central portion 54 disposed longitudinally between end portions 44 and 46. Crossing stent-graft 22 comprises a crossing support structure 56 and one or more crossing covering elements 58, which are securely attached to and cover at least partially cover first and second end portions 44 and 46. Central portion 54 is at least partially uncovered when crossing stent-graft 22 is in its radially-expanded state.

Typically, central portion 54 is completely uncovered. For some applications, as shown in the figures, the one or more crossing covering elements 58 include first and second covering elements 58A and 58B, which are securely attached to and at least partially cover first and second end portions 44 and 46, respectively. For some applications, when crossing stent-graft 22 is unconstrained in its radially-expanded state: (a) one end 60A of first covering element 58A defines a generally elliptical circumferential junction 62A between first end portion 44 and central portion 54, (b) one end 60B of second covering element 58B defines a generally elliptical circumferential junction 62A between second end portion 46 and central portion 54, and (c) central portion 54 is entirely uncovered.

Alternatively, central portion 54 is partially covered, e.g., less than 40%, such as less than 20% or less than 10% of a surface area thereof is covered when crossing stent-graft 22 is in its radially-expanded state. For example, the one or more crossing covering elements may comprise exactly one crossing covering element 58, a central portion of which extends along central portion 54 between end portions of the crossing covering element that cover first and second end portions 44 and 46, respectively.

For some applications, the one or more covering elements 58 do not extend to at least one of ends 44 and 46 of crossing stent-graft 202, such that support structure 56 is not covered near the end. For some applications, this uncovered portion is flared. The uncovered portion may facilitate proper fixation and sealing of the stent-graft with the blood vessel wall.

Crossing support structure 56 typically comprises a plurality of structural stent elements. For some applications, at least some of, e.g., all of, the structural stent elements are interconnected (as shown in the figures), while for other applications, at least a portion of, e.g., all, of the structural stent elements are not interconnected (configuration not shown). The one or more crossing covering elements serve as blood flow guides through at least a portion of first end portion 44 and at least a portion of second end portion 46, respectively.

For some applications, crossing stent-graft 22, when in its radially-expanded state, has an hour-glass shape, and central portion 54 is shaped so as to define a stricture in the hour-glass shape. Alternatively, for some applications, a perimeter of first end portion 44 varies by less than 20%, such as less than 10%, along a length thereof, when the crossing stent-graft is unconstrained in its radially-expanded state. Similarly, for some applications, a perimeter of second end portion 46 varies by less than 20%, such as less than 10%, along a length thereof, when the crossing stent-graft is unconstrained in its radially-expanded state.

For some applications, each of ends 48 and 50 of crossing stent-graft 22 has a perimeter of at least 3 cm, no more than 18 cm, and/or between 3 and 18 cm, when the crossing stent-graft is unconstrained in its radially-expanded state. For some applications, crossing stent-graft 22 has a total length L5 of at least 3 cm, no more than 20 cm, and/or between 3 and 20 cm, when unconstrained in its radially-expanded state. For some applications, central portion 54 has a length L6 of at least 3 cm, no more than 20 cm, and/or between 3 and 20 cm, when stent-graft 22 is unconstrained in its radially-expanded state. For some applications, first and second end portions 44 and 46 have respective lengths L7 and L8, each of which is at least 1 cm, no more than 10 cm, and/or between 1 and 10 cm, when stent-graft 22 is unconstrained in its radially-expanded state.

For some applications, a greatest perimeter P5 of central portion 54 is at least 1.5 cm, no more than 10 cm, and/or between 1.5 and 10 cm, such as at least 4.5 cm, no more than 8 cm, and/or between 4.5 and 8 cm, when crossing stent-graft 22 is unconstrained in its radially-expanded state. For some applications, a greatest perimeter of at least one of first end portion 44 and second end portion 46 is at least 6 cm, no more than 13 cm, and/or between 6 and 13 cm, when the crossing stent-graft is unconstrained in its radially-expanded state.

For some applications, an average perimeter of central portion 54 (a) is less than an average perimeter of first end portion 44 and (b) is less than an average perimeter of second end portion 46, when the crossing stent-graft is unconstrained in its radially-expanded state.

For some applications, fenestrated and/or crossing stent-grafts 20 and 22 implement one or more of the techniques described in the patent applications incorporated by reference hereinbelow. For example, the stent-grafts may utilize one or more of the configurations of aortic stent-grafts described in these patent applications.

For some applications, a perimeter of central portion 54 varies by less than 50% therealong, such as less than 30% therealong, or less than 20% therealong, when crossing stent-graft 22 is unconstrained in its radially-expanded state.

Reference is again made to FIGS. 2A-B, which show crossing stent-graft 22 passing through fenestrated stent-graft 20 (FIG. 2B shows the portion of crossing stent-graft 22 that is within fenestrated stent-graft). Fenestrated and crossing stent-grafts 20 and 22, when in their radially-expanded states, are sized and shaped such that, when crossing stent-graft 22 is disposed through first and second apertures 40 and 42 such that central portion 54 of crossing stent-graft 22 is within central portion 34 of fenestrated stent-graft 20, first and second end portions 44 and 46 of crossing stent-graft 22 pass through and form blood-impervious seals with first and second apertures 40 and 42, respectively. As a result, interior spaces defined by all of the following are in fluid communication with one another: first and the second end portions 24 and 26 and central portion 34 of fenestrated stent-graft 20, and first and second end portions 44 and 46 and central portion 54 of crossing stent-graft 22. Central portion 54 of crossing stent-graft 22 is generally sized to fit the perimeters P3 and P4 of apertures 40 and 42, when the stent-grafts are unconstrained in their radially-expanded states.

For some applications, when the crossing stent-graft is unconstrained in its radially-expanded state longitudinal length L1 of central portion 54 of crossing stent-graft 22 is at least 25%, no more than 120%, and/or between 25% and 120% of a closest distance D1 between apertures 40 and 42 (as labeled in FIG. 2B), such as at least 25%, no more than 100%, and/or between 25% and 100%. (Length L1 may be greater than distance D1 when the crossing stent-graft is unconstrained in its radially-expanded state, and central portion 54 may still be positioned entirely within fenestrated stent-graft 20, because the crossing stent-graft may longitudinally partially collapse and/or shorten when the stent-graft system is fully deployed.)

Reference is made to FIGS. 3A-H, which are schematic illustrations of an exemplary transluminal delivery procedure for implanting multi-component stent-graft system 10, in accordance with an application of the present invention. In this exemplary procedure, crossing stent-graft 22 is configured to be implanted in a main blood vessel having an aneurysm, such as a descending abdominal aorta 100 (in which the aneurysm is typically below the renal arteries, as shown). First and the second ends portions 24 and 26 of fenestrated stent-graft 20 are configured to be implanted at least partially in respective branching blood vessels of the main blood vessel, such as left and right renal arteries 102A and 102B. When the fenestrated stent-graft is thus implanted, central portion 34 of fenestrated stent-graft 20 is positioned in the main blood vessel, such as descending abdominal aorta 100, and first and second ends 28 and 30 are positioned in the branching blood vessels, such as left and right renal arteries 102A and 102B.

As shown in FIG. 3A, the exemplary procedure begins with the laparoscopic advancing of a guidewire 110 into a first branching blood vessel, such as left renal artery 102A, as shown, or right renal artery 102B (approach not shown).

Fenestrated stent-graft 20 is initially positioned in its radially-compressed state within a delivery shaft 120, typically near a distal end of the delivery shaft (e.g., such that at least one end of stent-graft 20 is within a distance of the distal end, which distance equals the sum of 2 cm and an axial length of the fenestrated stent-graft). As shown in FIG. 3B, delivery shaft 120 is laparoscopically advanced over guidewire 110 into left renal artery 102A, across descending abdominal aorta 100, and into right renal artery 102B. As a result, fenestrated stent-graft 20, while still in its radially-compressed state, is positioned such that first and second end portions 24 and 26 are at least partially disposed left and right renal arteries 102A and 102B, respectively (and ends 28 and 30 of stent-graft 20 are disposed in left and right renal arteries 102A and 102B, respectively). Central portion 34 is positioned at least partially within aorta 100, such as entirely with the aorta. Optionally, guidewire 110 is withdrawn, leaving delivery shaft 120 in place (approach not shown).

As shown in FIGS. 3C-D, the fenestrated stent-graft is held in place as delivery shaft 120 is withdrawn, thereby delivering the fenestrated stent-graft from the delivery shaft. Optionally, techniques for holding the fenestrated stent-graft in place may be used that are described in a PCT application filed Nov. 30, 2010, entitled, "Multi-component stent-graft system for implantation in a blood vessel with multiple branches," which is incorporated herein by reference, such as with reference to FIGS. 10 and 11A-E or FIGS. 12A-C thereof.

Fenestrated stent-graft 20 typically self-expands, until it assumes its radially-expanded state, upon reaching its maximum unconstrained size, and/or being constrained from further expansion by the wall of the blood vessels. FIG. 3C shows the fenestrated stent-graft in an intermediate state of expansion, while FIG. 3D shows the stent-graft fully expanded. First and second lateral apertures 40 and 42 are open within descending abdominal aorta 100, facing in generally radially opposing directions (first aperture 40 faces upstream, and second aperture 42 faces downstream). The guidewire is then withdrawn (alternatively, instead of delivering the stent-graft using this over-the-wire (OTW)

approach, the guidewire may be withdrawn before releasing the stent-graft from delivery shaft 120, as mentioned above).

As shown in FIG. 3E, a second guidewire 130 is advanced into the main blood vessel, e.g., descending abdominal aorta 100, typically transvascularly (typically percutaneously) via one of the iliac arteries. Guidewire 130 is passed through second opening 24 and first opening 40, such that the guidewire passes through central portion 34 of fenestrated stent-graft 20.

Crossing stent-graft 22 is initially positioned in its radially-compressed state within a delivery shaft 140, typically near a distal end of the delivery shaft (e.g., such that at least one end of stent-graft 22 is within a distance of the distal end, which distance equals the sum of 2 cm and an axial length of the crossing stent-graft). As shown in FIG. 3F, delivery shaft 140 is advanced over guidewire 130 through second and first openings 42 and 40. As a result, crossing stent-graft 22, while still in its radially-compressed state, is positioned such central portion 54 of crossing stent-graft 22 is positioned within central portion 34 of fenestrated stent-graft 20 (in aorta 100), and first and second end portions 44 and 46 of crossing stent-graft 22 pass through first and second apertures 40 and 42, respectively. First and second ends 48 and 50 are positioned in ascending aorta 100 upstream and downstream of the renal arteries, respectively. Optionally, guidewire 130 is withdrawn, leaving delivery shaft 140 in place (approach not shown).

Figure 3G:
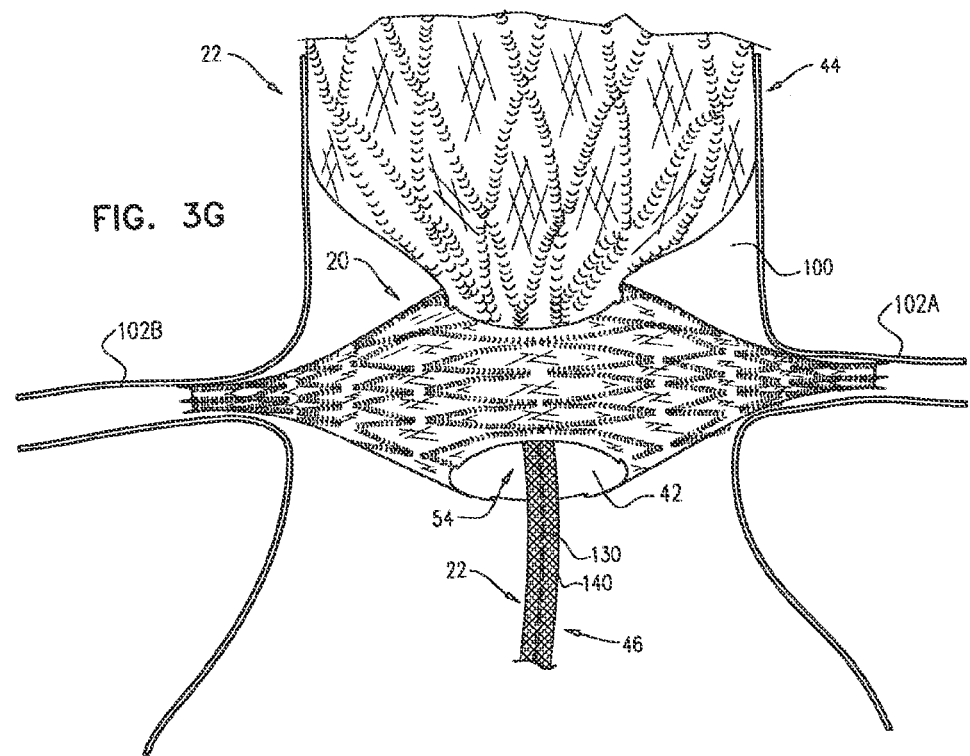

As shown in FIGS. 3G-H, the crossing stent-graft is held in place as delivery shaft 140 is withdrawn, thereby delivering the crossing stent-graft from the delivery shaft. Optionally, techniques for holding the fenestrated stent-graft in place may be used that are described in the above-mentioned PCT application filed Nov. 30, 2010, entitled, "Multi-component stent-graft system for implantation in a blood vessel with multiple branches," such as with reference to FIGS. 10 and 11A-E or FIGS. 12A-C thereof.

Crossing stent-graft 22 typically self-expands, until it assumes its radially-expanded state, upon reaching its maximum unconstrained size, and/or being constrained from further expansion by the wall of the aorta. FIG. 3G shows the crossing stent-graft in an intermediate state of expansion, in which first end portion 44 has radially expanded, while FIG. 3D shows the stent-graft fully expanded. First and second end portions 44 and 46 of crossing stent-graft 22 form blood-impervious seals with first and second apertures 40 and 42, respectively. As a result, interior spaces defined by all of the following are in fluid communication with one another: first and the second end portions 24 and 26 and central portion 34 of fenestrated stent-graft 20, and first and second end portions 44 and 46 and central portion 54 of crossing stent-graft 22. In the exemplary deployment shown in FIGS. 3A-3H, this fluid communication allows blood to flow down descending abdominal aorta 100, into first end portion 44 of crossing stent-graft 22, and then into both central portion 54 of crossing stent-graft 22 and central portion 34 of fenestrated stent-graft 20. From the central portions, (a) a portion of the blood flow branches to first and second end portions 24 of fenestrated stent-graft 20, and renal arteries 102A and 102B, and (b) a portion of the blood flow continues downstream to second end portion 46 of crossing stent-graft 22 and the sub-renal descending abdominal aorta (typically bypassing an aortic aneurysm in the sub-renal descending abdominal aorta).

The guidewire is then withdrawn (alternatively, instead of delivering the stent-graft using this over-the-wire (OTW) approach, the guidewire may be withdrawn before releasing the stent-graft from delivery shaft 120, as mentioned above, and using a rapid-exchange methodology).

Figure 4:
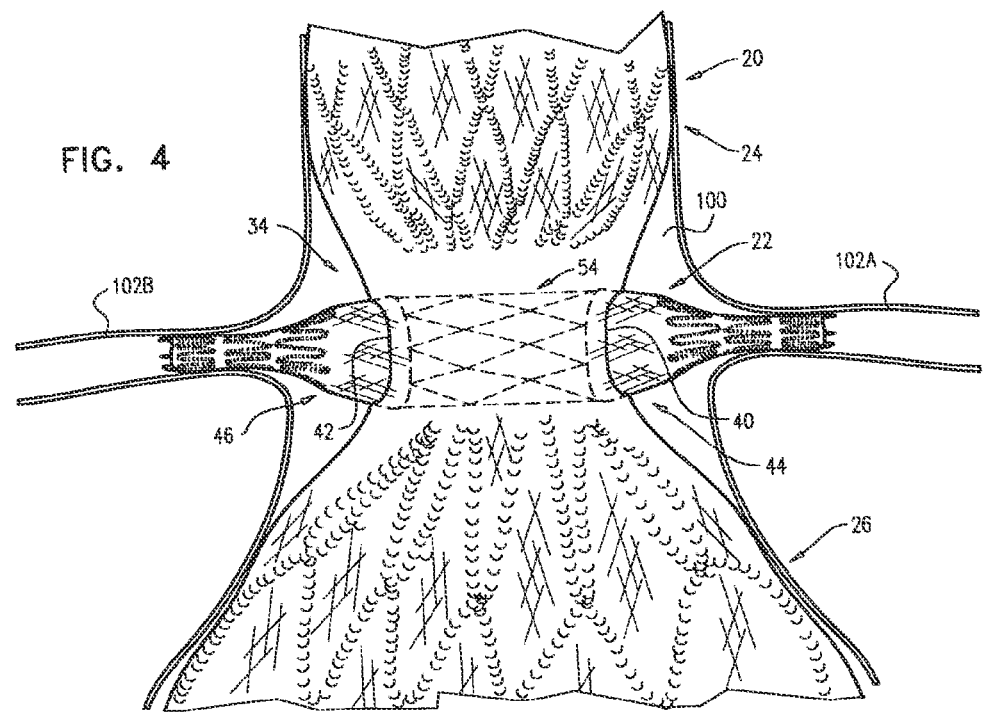
FIG. 4 is a schematic illustration of another deployment of the multi-component stent-graft system of FIGS. 1 and 2A-B, in accordance with an application of the present invention.

Reference is made to FIG. 4, which is a schematic illustration of another deployment of stent-graft system 10, in accordance with an application of the present invention. In this exemplary method of deploying system 10, fenestrated stent-graft 20 is deployed, e.g., endovascularly, in a main a blood vessel, such as descending abdominal aorta, such that first and second apertures 40 and 42 generally face first and second branching blood vessels of the main blood vessel, such as left and right renal arteries 102A and 102B. For some applications, fenestrated stent-graft 20 is deployed using techniques similar to those described hereinabove with reference to FIGS. 3E-H for deploying crossing stent-graft 22. FIG. 4 shows the fenestrated stent-graft is in its radially-expanded state, upon completion of deployment thereof.

After fenestrated stent-graft 20 has been deployed, crossing stent-graft 22 is introduced, e.g., laparoscopically, into the first branching blood vessel, e.g., the left or right renal artery (e.g., left renal artery 102A, as shown by way of example in FIG. 4). The crossing stent-graft, while in a radially-compressed state thereof, is passed through first and second apertures 40 and 42 of fenestrated stent-graft 20, and into the second branching blood vessel, e.g., the other of the left and right renal arteries (e.g., right renal artery 102B, as shown by way of example in FIG. 4), such that:

central portion 54 of crossing stent-graft 22 is within central portion 34 of fenestrated stent-graft 20, and first and second end portions 44 and 46 of crossing stent-graft 22 pass through first and second apertures 40 and 42, respectively.

For some applications, crossing stent-graft 22 is deployed using techniques similar to those described hereinabove with reference to FIGS. 3A-D for deploying fenestrated stent-graft 20.

Crossing stent-graft 22 is transitioned to its radially-expanded state (typically by deploying the crossing stent-graft from its delivery shaft). First and second end portions 44 and 46 of crossing stent-graft 22 form blood-impervious seals with first and second apertures 40 and 42, respectively. As a result, interior spaces defined by all of the following are in fluid communication with one another: first and second end portions 24 and 26 and central portion 34 of fenestrated stent-graft 20, and first and second end portions 44 and 46 and central portion 54 of crossing stent-graft 22.

Figure 5:
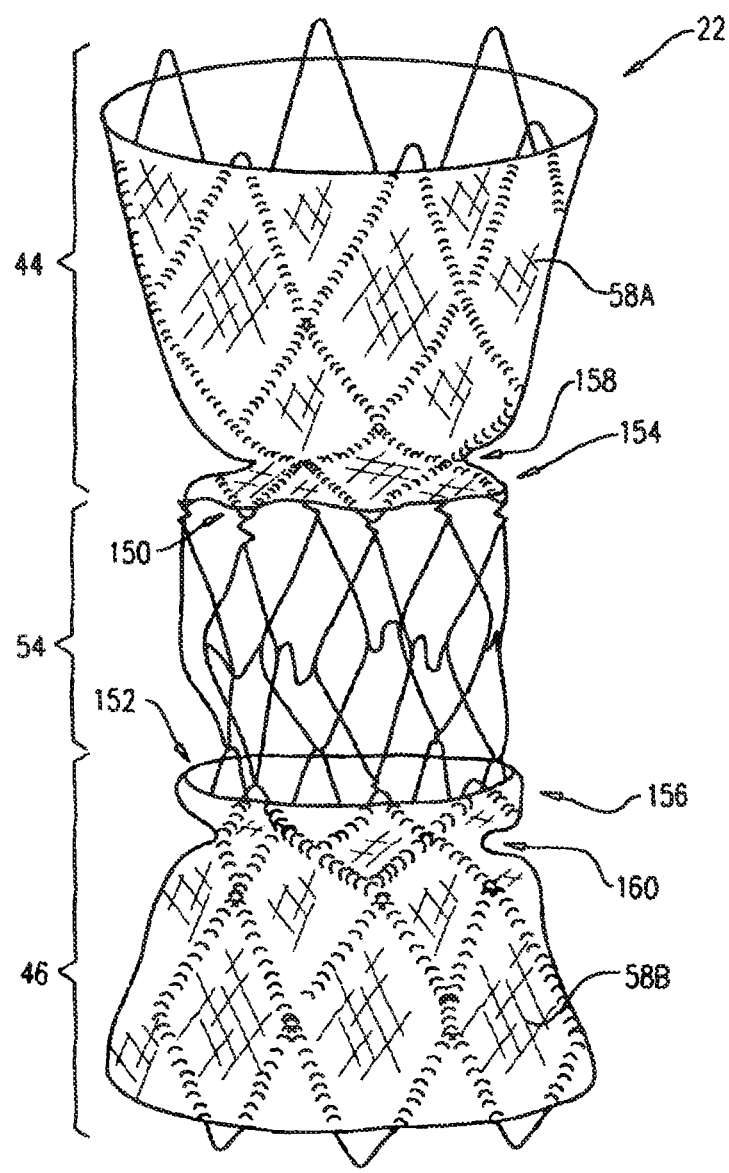
FIG. 5 is a schematic illustration of an alternative configuration of a crossing stent-graft of the multi-component stent-graft system of FIGS. 1 and 2A-B and/or FIG. 4, in accordance with an application of the present invention.

Reference is made to FIG. 5, which is a schematic illustration of an alternative configuration of crossing stent-graft 22, in accordance with an application of the present invention. This configuration of the crossing stent-graft may be used for any of the applications described above, including the applications described above with reference to FIGS. 1 and 2A-B, FIGS. 3A-H, and/or FIG. 4 (for use with the application described with reference to FIG. 4, the crossing stent-graft generally has the shape shown in FIG. 4, modified as described below).

In this configuration, first and second end portions 44 and 46 have medial ends 150 and 152, respectively, at which the first and second end portions are joined to the central portion, respectively. One or both of first and second end portions 44 and 46 are outwardly flared toward central portion 54, when the stent-graft is in its radially-expanded state, so as to define outward flares 154 and 156, respectively. Optionally, one or both of first and second end portions 44 and 46 are additionally slightly indented radially inward near the outward flares, away from central portion 54, so as to define radial indentations 158 and 160, respectively. Typically, first and second covering elements 58A and 58B at least partially, such as completely, cover the outward flares. The flares aid in proper axial positioning of crossing stent-graft 22 with respect to apertures 40 and 42 during deployment of the crossing stent-graft, by helping guide the crossing stent-graft into proper axial position. The flares may also help axially secure the crossing stent-graft to the fenestrated stent-graft by preventing axial movement of the crossing stent-graft with respect to the fenestrated stent-graft. In addition, the flares may help form the blood-impervious seals between first and second portions 44 and 46 of crossing stent-graft 22 and first and second apertures 40 and 42 of fenestrated stent-graft 20, as described hereinabove. The flared portions (together with radially-indented portions) may serve as interface members, and may generally have the shape of an hourglass. The radially-indented (narrower) portions may be sized to conform with the perimeters of apertures 40 and 42.

For some applications of the present invention, a kit is provided that comprises fenestrated stent-graft 20 and crossing stent-graft 22. For some applications, the kit further comprises delivery shaft 120, delivery shaft 140, guidewire 110, and/or guidewire 130.

For some applications, at least one of stent-grafts 20 and 22 comprises one or more anchoring elements that extend radially outwardly when the stent-graft assumes its radially-expanded state. The anchoring elements anchor the stent-graft to a vascular wall, helping prevent dislodgement.

For some applications, stent-graft system 10 is used to treat an aneurysm, such as an aortic aneurysm, or an aneurysm of another blood vessel. For example, the aneurysm may be of the sub-renal aorta, as shown in FIGS. 3A-H and 4. For some applications, a method is provided that comprises identifying that a patient suffers from an aneurysm, such as an aortic aneurism, and, responsively to the identifying, implanting (for example, including, transvascularly and/or laparoscopically introducing) one or more of the stent-grafts described herein, such as fenestrated stent-graft 20 and/or crossing stent-graft 22. Techniques for identifying that a patient suffers from an aneurism are well known, and thus not described herein.

Although stent-graft system 10 has sometimes been described hereinabove as being deployed in the descending abdominal aorta and the left and right renal arteries, the stent-graft system may, for some applications, also be deployed at other branching body lumens. For example, the main body lumen may be the aorta, and the branching body lumen may include the inferior or superior mesenteric arteries, or the celiac artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al.

U.S. application Ser. No. 12/529,936, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, entitled, "Multi-component stent-graft system for implantation in a blood vessel with multiple branches," which published as PCT Publication WO 2011/064782

PCT Application PCT/IL2010/001018, filed Dec. 2, 2010, entitled, "Endovascular fenestrated stent-grafting," which published as PCT Publication WO 2011/067764

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular stent-graft system, which comprises:
   a fenestrated stent-graft, which includes first and second end portions and a central portion disposed longitudinally therebetween, and which comprises a fenestrated support structure and a fenestrated covering element, which is securely attached to and covers at least a portion of the fenestrated support structure, wherein the fenestrated support structure and the fenestrated covering element are shaped so as to together define first and second lateral apertures in the central portion, which apertures face in generally radially opposing directions, when the fenestrated stent-graft is in a radially-expanded state thereof; and
   a crossing stent-graft, which includes first and second end portions and a central portion disposed longitudinally therebetween, and which comprises a crossing support structure and one or more crossing covering elements, which are securely attached to and at least partially cover the first and the second end portions, such that the central portion is at least partially uncovered when the crossing stent-graft is in a radially-expanded state thereof,
   wherein the fenestrated and the crossing stent-grafts are sized and shaped such that, when the crossing stent-graft is disposed through the first and the second apertures such that the central portion of the crossing stent-graft is within the central portion of the fenestrated stent-graft, the first and the second end portions of the crossing stent-graft (a) pass through the first and the second apertures, respectively, and (b) when the fenestrated and the crossing stent-grafts are in their radially-expanded states, form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft, and
   wherein the crossing stent-graft, when in its radially-expanded state, has an hour-glass shape, and the central portion of the crossing stent-graft is shaped so as to define a stricture in the hour-glass shape.

2. The apparatus according to claim 1, wherein the central portion of crossing stent-graft is generally sized to fit a perimeter of each of the apertures, when the stent-grafts are unconstrained in their radially-expanded states.

3. The apparatus according to claim 1, wherein the one or more crossing covering elements include first and second covering elements, which are securely attached to and at least partially cover the first and the second end portions of the crossing stent-graft, respectively.

4. Apparatus comprising an endovascular stent-graft system, which comprises:
   a fenestrated stent-graft, which includes first and second end portions and a central portion disposed longitudinally therebetween, and which comprises a fenestrated support structure and a fenestrated covering element, which is securely attached to and covers at least a portion of the fenestrated support structure, wherein the fenestrated support structure and the fenestrated covering element are shaped so as to together define first and second lateral apertures in the central portion, which apertures face in generally radially opposing directions, when the fenestrated stent-graft is in a radially-expanded state thereof; and
   a crossing stent-graft, which includes first and second end portions and a central portion disposed longitudinally therebetween, and which comprises a crossing support structure and one or more crossing covering elements, which are securely attached to and at least partially cover the first and the second end portions, such that the central portion is at least partially uncovered when the crossing stent-graft is in a radially expanded state thereof,
   wherein the fenestrated and the crossing stent-grafts are sized and shaped such that, when the crossing stent-graft is disposed through the first and the second apertures such that the central portion of the crossing stent-graft is within the central portion of the fenestrated stent-graft, the first and the second end portions of the crossing stent-graft (a) pass through the first and the second apertures, respectively, and (b) when the fenestrated and the crossing stent-grafts are in their radially-expanded states, form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft,
   wherein the one or more crossing covering elements include first and second covering elements, which are securely attached to and at least partially cover the first and the second end portions of the crossing stent-graft, respectively, and
   wherein, when the crossing stent-graft is unconstrained in its radially-expanded state:
   one end of the first covering element defines a generally elliptical circumferential junction between the first end portion and the central portion of the crossing stent-graft,
   one end of the second covering element defines a generally elliptical circumferential junction between the second end portion and the central portion of the crossing stent-graft, and
   the central portion of the crossing stent-graft is entirely uncovered.

5. The apparatus according to claim 1, wherein the central portion of the fenestrated stent-graft is generally fusiform, when the fenestrated stent-graft is unconstrained in its radially-expanded state.

6. The apparatus according to claim 1, wherein the fenestrated stent-graft is generally fusiform, when the fenestrated stent-graft is unconstrained in its radially-expanded state.

7. Apparatus comprising an endovascular stent-graft system, which comprises:
   a fenestrated stent-graft, which includes first and second end portions and a central portion disposed longitudinally therebetween, and which comprises a fenestrated support structure and a fenestrated covering element, which is securely attached to and covers at least a portion of the fenestrated support structure, wherein the fenestrated support structure and the fenestrated covering element are shaped so as to together define first and second lateral apertures in the central portion, which apertures face in generally radially opposing directions, when the fenestrated stent-graft is in a radially-expanded state thereof; and
   a crossing stent-graft, which includes first and second end portions and a central portion disposed longitudinally therebetween, and which comprises a crossing support structure and one or more crossing covering elements, which are securely attached to and at least partially cover the first and the second end portions, such that the central portion is at least partially uncovered when the crossing stent-graft is in a radially expanded state thereof,
   wherein the fenestrated and the crossing stent-grafts are sized and shaped such that, when the crossing stent-graft is disposed through the first and the second apertures such that the central portion of the crossing stent-graft is within the central portion of the fenestrated stent-graft, the first and the second end portions of the crossing stent-graft (a) pass through the first and the second apertures, respectively, and (b) when the fenestrated and the crossing stent-grafts are in their radially-expanded states, form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft, and
   wherein the first and the second end portions of the crossing stent-graft have respective medial ends, at which the first and the second end portions are joined to the central portion of the crossing stent-graft, respectively, and wherein at least one of the first and the second end portions of the crossing stent-graft is outwardly flared toward the central portion of the crossing stent-graft, when the crossing stent-graft is in its radially-expanded state.

8. Apparatus comprising an endovascular stent-graft system, which comprises:
   a fenestrated stent-graft, which includes first and second end portions and a central portion disposed longitudinally therebetween, and which comprises a fenestrated support structure and a fenestrated covering element, which is securely attached to and covers at least a portion of the fenestrated support structure, wherein the fenestrated support structure and the fenestrated covering element are shaped so as to together define first and second lateral apertures in the central portion, which apertures face in generally radially opposing directions, when the fenestrated stent-graft is in a radially-expanded state thereof; and a crossing stent-graft, which includes first and second end portions and a central portion disposed longitudinally therebetween, and which comprises a crossing support structure and one or more crossing covering elements, which are securely attached to and at least partially cover the first and the second end portions, such that the central portion is at least partially uncovered when the crossing stent-graft is in a radially expanded state thereof, wherein the fenestrated and the crossing stent-grafts are sized and shaped such that, when the crossing stent-graft is disposed through the first and the second apertures such that the central portion of the crossing stent-graft is within the central portion of the fenestrated stent-graft, the first and the second end portions of the crossing stent-graft (a) pass through the first and the second apertures, respectively, and (b) when the fenestrated and the crossing stent-grafts are in their radially-expanded states, form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft, and wherein the first and the second end portions of the fenestrated stent-graft have respective ends that coincide with respective ends of the fenestrated stent-graft, and wherein a ratio of (a) a greatest perimeter of the central portion of the fenestrated stent-graft to (b) a perimeter of each of the ends of the first and the second end portions of the fenestrated stent-graft is between 4 and 15, when the fenestrated stent-graft is unconstrained in its radially-expanded state.

9. The apparatus according to claim 1, wherein the fenestrated covering element does not extend to at least one end of the fenestrated stent-graft, such that the fenestrated support structure is not covered near the end.

10. The apparatus according to claim 1, wherein the one or more crossing covering elements do not extend to at least one end of the crossing stent-graft, such that the crossing support structure is not covered near the end.

11. The apparatus according to claim 1, wherein an average perimeter of the central portion of the crossing stent-graft (a) is less than an average perimeter of the first end portion of the crossing stent-graft and (b) is less than an average perimeter of the second end portion of the crossing stent-graft, when the crossing stent-graft is unconstrained in its radially-expanded state.

12. The apparatus according to claim 8, wherein the crossing stent-graft, when in its radially-expanded state, has an hour-glass shape, and the central portion of the crossing stent-graft is shaped so as to define a stricture in the hour-glass shape.

13. The apparatus according to claim 1, wherein the crossing stent-graft is configured to be implanted in a main blood vessel having an aneurysm, and the first and the second end portions of the fenestrated stent-graft are configured to be implanted at least partially in respective branching blood vessels of the main blood vessel, such that the central portion of the fenestrated stent-graft is positioned in the main blood vessel.

14. The apparatus according to claim 1, wherein the fenestrated stent-graft is configured to be implanted in a main blood vessel having an aneurysm, and the first and the second end portions of the crossing stent-graft are configured to be implanted at least partially in respective branching blood vessels of the main blood vessel, such that the central portion of the crossing stent-graft is positioned in the main blood vessel.

15. A method for treating a patient, the method comprising:

providing (a) a fenestrated stent-graft, which includes first and second end portions and a central portion disposed longitudinally therebetween, which central portion is shaped so as to define first and second lateral apertures that face in generally radially opposing directions, when the fenestrated stent-graft is in a radially-expanded state thereof, and (b) a crossing stent-graft, which includes first and second end portions and a central portion disposed longitudinally therebetween, and which comprises a crossing support structure and one or more crossing covering elements, which are securely attached to and at least partially cover the first and the second end portions, such that the central portion is at least partially uncovered when the crossing stent-graft is in a radially-expanded state thereof;

deploying the fenestrated stent-graft such that the first and the second end portions thereof are at least partially positioned in respective first and second branching blood vessels of a main blood vessel of the patient, the central portion of the fenestrated stent-graft is positioned in the main blood vessel, and the fenestrated stent-graft is in its radially-expanded state;

thereafter, introducing the crossing stent-graft into the main blood vessel, and passing the crossing stent-graft, while in a radially-compressed state thereof, through the second and the first apertures, such that the central portion of the crossing stent-graft is within the central portion of the fenestrated stent-graft, and the first and the second end portions of the crossing stent-graft pass through the first and the second apertures, respectively; and transitioning the crossing stent-graft to its radially-expanded state, such that the first and the second end portions of the crossing stent-graft form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft.

16. The method according to claim 15, wherein deploying the fenestrated stent-graft comprises laparoscopically introducing the fenestrated stent-graft into the first branching blood vessel, and advancing the fenestrated stent-graft across the main blood vessel to the second branching blood vessel.

17. The method according to claim 15, wherein introducing the crossing stent-graft comprises endovascularly introducing the crossing stent-graft into the main blood vessel.

18. The method according to claim 15, wherein providing the fenestrated stent-graft comprises providing the fenestrated stent-graft in which the central portion thereof is generally fusiform, when the fenestrated stent-graft is unconstrained in its radially-expanded state.

19. The method according to claim 15, wherein providing the fenestrated stent-graft comprises providing the fenestrated stent-graft which is generally fusiform, when the fenestrated stent-graft is unconstrained in its radially-expanded state.

20. A method for treating a patient, the method comprising:

providing (a) a fenestrated stent-graft, which includes first and second end portions and a central portion disposed longitudinally therebetween, which central portion is shaped so as to define first and second lateral apertures that face in generally radially opposing directions, when the fenestrated stent-graft is in a radially-expanded state thereof, and (b) a crossing stent-graft, which includes first and second end portions and a central portion disposed longitudinally therebetween, and which comprises a crossing support structure and one or more crossing covering elements, which are securely attached to and at least partially cover the first and the second end portions, such that the central portion is at least partially uncovered when the crossing stent-graft is in a radially-expanded state thereof;

deploying the fenestrated stent-graft in a main blood vessel of the patient such that the first and the second apertures generally face first and second branching blood vessels of the main blood vessel, and the fenestrated stent-graft is in its radially-expanded state;

thereafter, introducing the crossing stent-graft into the first branching blood vessel, and passing the crossing stent-graft, while in a radially-compressed state thereof, through the first and the second apertures, and into the second branching blood vessel, such that the central portion of the crossing stent-graft is within the central portion of the fenestrated stent-graft, and the first and the second end portions of the crossing stent-graft pass through the first and the second apertures, respectively; and transitioning the crossing stent-graft to its radially-expanded state, such that the first and the second end portions of the crossing stent-graft form blood-impervious seals with the first and the second apertures, respectively, such that interior spaces defined by all of the following are in fluid communication with one another: the first and the second end portions and the central portion of the fenestrated stent-graft, and the first and the second end portions and the central portion of the crossing stent-graft.

21. The method according to claim 20, wherein deploying the fenestrated stent-graft comprises endovascularly introducing the crossing stent-graft into the main blood vessel.

22. The method according to claim 20, wherein introducing the crossing stent-graft comprises laparoscopically introducing the crossing stent-graft into the first branching blood vessel, and advancing the crossing stent-graft across the main blood vessel to the second branching blood vessel.

23. The method according to claim 15, wherein providing the crossing stent-graft comprises providing the crossing stent-graft in which the central portion thereof is generally sized to fit a perimeter of each of the apertures, when the stent-grafts are unconstrained in their radially-expanded states.

24. The method according to claim 20, wherein providing the crossing stent-graft comprises providing the crossing stent-graft in which the central portion thereof is generally sized to fit a perimeter of each of the apertures, when the stent-grafts are unconstrained in their radially-expanded states.

* * * * *